US012329516B2

(12) United States Patent
Jagannathan et al.

(10) Patent No.: US 12,329,516 B2
(45) Date of Patent: *Jun. 17, 2025

(54) SYSTEMS AND METHODS FOR ASSESSING GAIT, STABILITY, AND/OR BALANCE OF A USER

(71) Applicant: PLETHY, INC., San Jose, CA (US)

(72) Inventors: Ravi Jagannathan, San Jose, CA (US); Raja Sundaram, Los Gatos, CA (US); Sahadevan Harikrishnan, Fremont, CA (US)

(73) Assignee: Plethy, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/582,529

(22) Filed: Feb. 20, 2024

(65) Prior Publication Data

US 2024/0268710 A1 Aug. 15, 2024

Related U.S. Application Data

(63) Continuation of application No. 17/771,796, filed as application No. PCT/US2020/056459 on Oct. 20, (Continued)

(51) Int. Cl.
*A61B 5/00* (2006.01)
*A61B 5/11* (2006.01)
(Continued)

(52) U.S. Cl.
CPC .......... *A61B 5/1128* (2013.01); *A61B 5/1121* (2013.01); *A61B 5/721* (2013.01); (Continued)

(58) Field of Classification Search
None
See application file for complete search history.

(56) References Cited

U.S. PATENT DOCUMENTS 5,497,787 A    3/1996   Nemesdy et al.
5,991,654 A    11/1999  Tumey et al.
(Continued)

FOREIGN PATENT DOCUMENTS

CN    102214309 A    10/2011
CN    107862302 A    3/2018
(Continued)

OTHER PUBLICATIONS

Di Biase, Lazzaro, Alessandro Di Santo, Maria Letizia Caminiti, Alfredo De Liso, Syed Ahmar Shah, Lorenzo Ricci, and Vincenzo Di Lazzaro. "Gait analysis in Parkinson's disease: An overview of the most accurate markers for diagnosis and symptoms monitoring." Sensors 20,12. Published Jun. 22, 2020. (Year: 2020).*
(Continued)

*Primary Examiner* — Vincent Gonzales
(74) *Attorney, Agent, or Firm* — Aurora Consulting LLC; Kristen J. Hansen; Ashley Sloat

(57) ABSTRACT

A method for assessing movement of a body portion includes, via one or more machine learning models, analyzing a sensor signal indicative of movement of the body portion to determine a movement of the body portion; determining a sensor confidence level based, at least in part, on a characteristic of the sensor signal; receiving a series of images indicative of movement of the body portion; measuring an angle of movement of the body portion; determining a vision confidence level based, at least in part, on a quality of an identification the body portion; selecting the sensor signal, the measured angle of movement, or a combination thereof as an input into a machine learning model based on the sensor confidence level and the vision confidence level, respectively; analyzing the input to determine a movement pattern of the body portion; and outputting the movement pattern to a user.

20 Claims, 23 Drawing Sheets

Knee and hip joint

Related U.S. Application Data 2020, now Pat. No. 11,950,901, which is a continuation of application No. 16/664,379, filed on Oct. 25, 2019, now Pat. No. 10,842,415.

(51) Int. Cl.
| | |
|---|---|
| *A63B 24/00* | (2006.01) |
| *G06N 3/08* | (2023.01) |
| *G06N 20/00* | (2019.01) |
| *G16H 30/20* | (2018.01) |

(52) U.S. Cl.
CPC ........ *A61B 5/7267* (2013.01); *A63B 24/0062* (2013.01); *G06N 3/08* (2013.01); *G06N 20/00* (2019.01); *G16H 30/20* (2018.01); *A61B 5/0077* (2013.01); *A61B 2562/0219* (2013.01); *A61B 2576/00* (2013.01)

(56) References Cited

U.S. PATENT DOCUMENTS

| | | | |
|---|---|---|---|
| 6,047,203 | A | 4/2000 | Sackner et al. |
| 6,381,482 | B1 | 4/2002 | Jayaraman et al. |
| 6,941,775 | B2 | 9/2005 | Sharma |
| 6,980,853 | B2 | 12/2005 | Miyoshi et al. |
| 7,191,803 | B2 | 3/2007 | Orr et al. |
| 7,319,895 | B2 | 1/2008 | Klefstad-Sillonville et al. |
| 7,474,910 | B2 | 1/2009 | Hassonjee et al. |
| 7,559,902 | B2 | 7/2009 | Ting et al. |
| 7,849,888 | B2 | 12/2010 | Karayianni et al. |
| 8,146,171 | B2 | 4/2012 | Chung et al. |
| 8,403,881 | B2 | 3/2013 | Ferren et al. |
| 8,409,132 | B2 | 4/2013 | Ferren et al. |
| 8,551,008 | B2 | 10/2013 | Naghavi et al. |
| 8,585,602 | B2 | 11/2013 | Crabtree et al. |
| 8,597,194 | B2 | 12/2013 | Barak |
| 8,636,670 | B2 | 1/2014 | Ferren et al. |
| 8,870,813 | B2 | 10/2014 | Ferren et al. |
| 8,925,392 | B2 | 1/2015 | Esposito et al. |
| 9,186,092 | B2 | 11/2015 | Mestrovic et al. |
| 9,459,089 | B2 | 10/2016 | Ganton et al. |
| 10,929,829 | B1 * | 2/2021 | Hazelwood ............ H04N 7/183 |
| 2005/0059903 | A1 | 3/2005 | Izumi |
| 2007/0225614 | A1 | 9/2007 | Naghavi et al. |
| 2009/0079559 | A1 | 3/2009 | Dishongh et al. |
| 2009/0234262 | A1 | 9/2009 | Reid, Jr. et al. |
| 2009/0309579 | A1 | 12/2009 | Cochran |
| 2010/0137701 | A1 | 6/2010 | Papastefanou |
| 2010/0208063 | A1 | 8/2010 | Lee et al. |
| 2010/0240967 | A1 | 9/2010 | Kim et al. |
| 2010/0292549 | A1 | 11/2010 | Shuler |
| 2011/0060252 | A1 | 3/2011 | Simonsen et al. |
| 2012/0065561 | A1 | 3/2012 | Ballas et al. |
| 2012/0123802 | A1 | 5/2012 | Feldman et al. |
| 2012/0173319 | A1 | 7/2012 | Ferrara |
| 2012/0179020 | A1 | 7/2012 | Wekell |
| 2014/0088461 | A1 | 3/2014 | Mack et al. |
| 2014/0257836 | A1 | 9/2014 | Walker et al. |
| 2015/0019135 | A1 | 1/2015 | Kacyvenski et al. |
| 2015/0269825 | A1 | 9/2015 | Tran |
| 2015/0351698 | A1 | 12/2015 | Cronin |
| 2016/0015297 | A1 | 1/2016 | Strauss et al. |
| 2016/0081594 | A1 | 3/2016 | Gaddipati et al. |
| 2016/0232322 | A1 | 8/2016 | Mensinger et al. |
| 2016/0242646 | A1 | 8/2016 | Obma |
| 2016/0278642 | A1 | 9/2016 | Vogel et al. |
| 2016/0302721 | A1 | 10/2016 | Wiedenhoefer et al. |
| 2016/0367406 | A1 | 12/2016 | Barnett |
| 2017/0020765 | A1 * | 1/2017 | Lim .................. A61H 3/00 |
| 2017/0049394 | A1 | 2/2017 | Zhang et al. |
| 2017/0140121 | A1 | 5/2017 | Schulhauser et al. |
| 2018/0132758 | A1 * | 5/2018 | Benford ................ A61B 5/112 |
| 2019/0049968 | A1 | 2/2019 | Dean et al. |
| 2019/0139297 | A1 | 5/2019 | Chen |
| 2019/0159954 | A1 * | 5/2019 | Ozsecen ................ B25J 9/0006 |
| 2019/0228330 | A1 | 7/2019 | Kaifosh et al. |
| 2019/0318194 | A1 | 10/2019 | Liu et al. |
| 2020/0000373 | A1 | 1/2020 | Agrawal et al. |

FOREIGN PATENT DOCUMENTS

| | | |
|---|---|---|
| WO | 9300042 A1 | 1/1993 |
| WO | 2005067796 A1 | 7/2005 |
| WO | 2009125327 A1 | 10/2009 |
| WO | 2010088696 A1 | 8/2010 |
| WO | 2011137515 A1 | 11/2011 |
| WO | 2013030709 A2 | 3/2013 |
| WO | 2014207653 A1 | 12/2014 |
| WO | 2016110804 A1 | 7/2016 |
| WO | 2016174659 A1 | 11/2016 |
| WO | 2019147928 A1 | 8/2019 |

OTHER PUBLICATIONS

Poon, Carmen CY, Benny PL Lo, Mehmet Rasit Yuce, Akram Alomainy, and Yang Hao. "Body sensor networks: In the era of big data and beyond." IEEE reviews in biomedical engineering 8 (2015): 4-16. (Year: 2015).*

Extended European Search Report dated Nov. 8, 2023 re EP20880062. 3-1113 / 4048148 PCT/US2020056459.

International Search Report dated Jan. 3, 2019 from International Application PCT/US2018/55384, 2 pgs.

International Search Report dated Mar. 24, 2017 from International Application PCT/US2016/63419, 3 pgs.

Written Opinion dated Mar. 24, 2017 from International Application PCT/US2016/63419, 10 pgs.

Potluri, et al. article titled "Machine Learning based Human Gait Segmentation with Wearable Sensor Platform," 2019 41st Annual International Conference of the IEEE Engineering in Medicine and Biology Society (EMBC), IEEE, [Online] Jul. 23, 2019 (Jul. 23, 2019), pp. 588-594, XP033625415, DOI: 10.1109/EMBC.2019. 8857509.

Rong-Hao Liang; Bin Yu; Mengru Xue; Jun Hu; Loe M G Feijs, "BioFidget: Biofeedback for Respiration Training Using an Augmented Fidget Spinner", Human Factors in Computing Systems,, pp. 1-12, URL: https://www.drhu.eu/publications/2018-CHI-BioFidget. pdf, (Dec. 8, 2020), XP058402910.

S. Prasad and L. M. Bruce, "Decision fusion with confidence-based weight assignment", IEEE Trans. on Geoscience and Remote Sensing 46, No. 5, May 2008, pp. 1448-1456. (Year: 2008).

V. Kyriazis, "Gait analysis techniques", J. Orthopaed. Traumatol. 1, 2001, pp. 1-6. (Year: 2001).

Written Opinion dated Jan. 3, 2019 from International Application PCT/US2018/55384, 8 pgs.

Left Blank.

* cited by examiner

Knee and hip joint

Pelvic joint

Toe joint

SYSTEMS AND METHODS FOR ASSESSING GAIT, STABILITY, AND/OR BALANCE OF A USER

CROSS-REFERENCE TO RELATED APPLICATIONS

This application is a continuation of U.S. patent application Ser. No. 17/771,796, filed Apr. 25, 2022, which is a 35 U.S.C 371 National Stage filing for PCT Application Ser. No. PCT/US2020/056459, filed Oct. 20, 2020, now published as WO 2021/080967, which claims priority to U.S. patent application Ser. No. 16/664,379, filed on Oct. 25, 2019, now U.S. Pat. No. 10,842,415 issued Nov. 24, 2020, the contents of each of which are herein incorporated by reference in their entireties.

TECHNICAL FIELD

This disclosure relates to the fields of health and wellness, and more specifically, to devices, systems, and methods for digitally monitoring one or more health indicators of an individual, including circumferential changes to one or more body portions.

BACKGROUND

As people live longer, musculoskeletal health is a leading indicator for acute and chronic health conditions. Precise tracking and analysis of joint movement, gait and other aspects including bilateral deviations in movement can enable the assessment and maintenance of overall wellness and assist in recovery from injuries, as well as assessment of health before and after a surgical or injury episode. Gait analysis is a key indicator of musculoskeletal health and neurological conditions and also is a vital part of pre/post-surgical assessment in orthopedic medicine. In each of the above scenarios, monitoring any combination of movement and gait may provide valuable insights into the health or wellness of an individual.

Current systems that claim to monitor or assess gait do not collect sufficient data from enough sources to be able to make clear determinations of gait, balance, and/or stability. Further, collecting increasing amounts of data presents new issues for analysis to arrive at meaningful conclusions about a patient's gait, balance, and/or stability. For example, some systems only collect data from sensors positioned in a user's shoes or a belt around a user's waist. These systems fail to achieve an accurate, global picture of user movement contributing to gait, balance, and stability. Other systems use reflective tape at various body locations to measure and assess movement. These systems cannot account for scenarios in which the processor cannot locate a body portion. Typically, in such scenarios, the processor "guesses" where the body portion is located, which may be erroneous and result in inaccurate gait, balance, and/or stability assessment. Further, gait, balance, and stability vary drastically from user to user and within the same user over time. Currently available systems do not have the mechanisms in place to adapt the analysis over time to account for such changes in a user or across users over time.

Accordingly, there exists a need to provide improved systems and methods for measuring and analyzing gait, balance, and/or stability. Provided herein are such systems and methods.

BRIEF DESCRIPTION OF THE DRAWINGS

The foregoing is a summary, and thus, necessarily limited in detail. The above-mentioned aspects, as well as other aspects, features, and advantages of the present technology will now be described in connection with various embodiments, with reference made to the following accompanying drawings:

FIG. 4A illustrates an exemplary, non-limiting cervical, lumbar, hip, and leg sensor placement. FIG. 4B illustrates an exemplary, non-limiting cervical sensor placement.

FIG. 5A illustrates a slap gait. FIG. 5B illustrates a Trendelenburg gait. FIG. 5C illustrates a one-sided Trendelenburg gait. FIG. 5D illustrates a diplegic gait. FIG. 5E illustrates a short swing gait. FIG. 5F illustrates an ataxic wide base gait. FIGS. 5F-5H illustrate an inefficient gait stance from a side view and posterior view, respectively. FIG. 5I illustrates heel eversion.

FIG. 9A illustrates various planes of movement with respect to a frontal plan. FIG. 9B illustrates various planes of movement with respect to a sagittal plane. FIG. 9C illustrates various planes of movement with respect to a transverse plane.

FIG. 10A illustrates plantar flexion. FIG. 10B illustrates normal movement and movement indicative of Trendelenburg gait. FIG. 10C illustrates hip and knee joint and leg movement.

FIG. 12A illustrates an example input image from an image sensor. FIG. 12B illustrates a preprocessed image. FIG. 12C illustrates pixel level segmentation of an identified body portion in the image. FIG. 12D illustrates a stick figure reduction of the image to determine movement of the identified body portion in the image.

Figure 1:
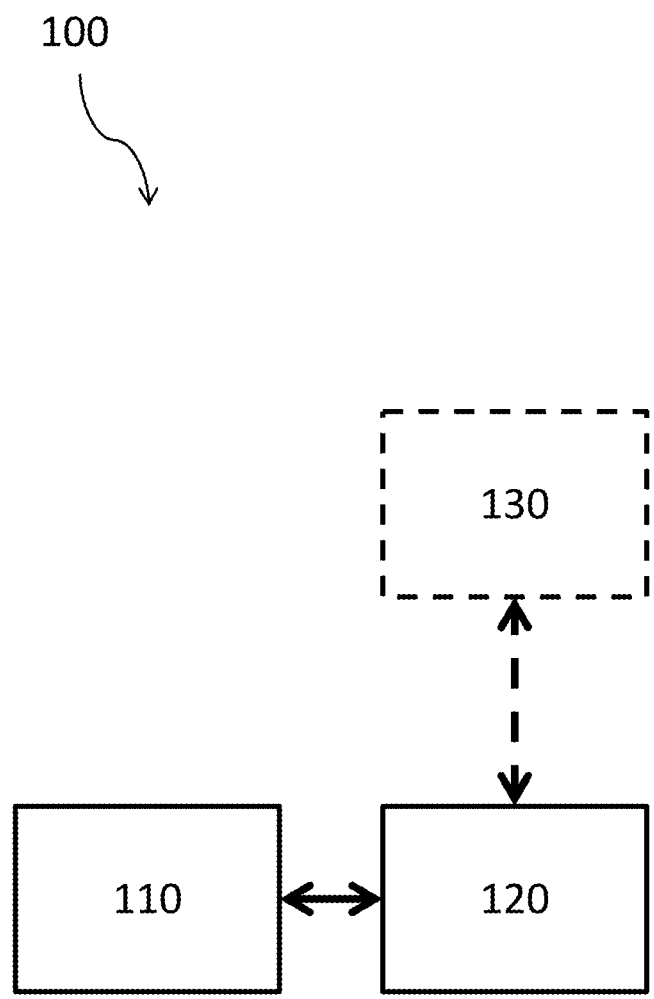
FIG. 1 illustrates a schematic block diagram of one embodiment of a system for monitoring gait, stability, and/or balance of an individual.

The illustrated embodiments are merely examples and are not intended to limit the invention.

DETAILED DESCRIPTION

The following description is not intended to limit the invention to these described embodiments, but rather to enable any person skilled in the art to make and use this invention. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Throughout and within this specification, one or more publications may be referenced to more fully describe the state of the art. The disclosures of each of these references are incorporated herein by reference in their entireties as though they also form part of this disclosure.

Unless otherwise defined, each technical or scientific term used herein has the same meaning as commonly understood by one of ordinary skill in the art to which this disclosure belongs.

As used in the description and claims, the singular form "a", "an" and "the" include both singular and plural references unless the context clearly dictates otherwise. For example, the term "a limb" may include, and is contemplated to include, a plurality of limbs. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., a change in force or circumference), indicates approximations which may vary, for example, by (+) or (−) 5%. All numerical ranges provided herein are inclusive of the stated start and end numbers. The term "substantially" indicates mostly (i.e., greater than 50%) or essentially all of an element, process, component, device, or system.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

There is a need for improved means for monitoring musculoskeletal health conditions of individuals (e.g., gait, balance, stability, etc.) as part of the health care regime or provider prescribed care plan. In particular, there is a need for devices, systems, and methods that can monitor and precisely track and analyze joint movements, balance, stability, and gait allowing overall assessment of wellness and assist in health preparation before and after a surgical or injury episode. There is also a need, more generally, for devices, systems, and methods that can detect joint movements, balance, stability, and gait and adaptively adjust a care protocol to the daily needs of the patient. The present disclosure is directed to devices, systems, and methods that fill one or more of these needs.

Previous systems that sought to measure gait focused either on sensor data or image data. For example, gait was measured using sensors positioned in foot-worn clothing or apparatuses, sensors mounted on or in a track (e.g., treadmill track), sensors positioned on a few select body areas, or sensors mounted on or in a belt. Other systems used images, for example using high frame rate cameras or video, to monitor and analyze user movement and gait. Such systems in isolation failed to accurately measure user movement. At least one study compared gait measurement reliability using either inertial motion capture or optical motion capture (See: Cloete T and Scheffer C. "Benchmarking of a full-body inertial motion capture system for clinical gait analysis." 30th Annual International IEEE EMBS Conference: Vancouver, British Columbia, Canada. Aug. 20-24, 2008). This study and others highlight the need for better, more reliable gait measurement and assessment systems and methods.

Patent publication KR20190014641A describes a walking sensing device including a three-axis gyroscope sensor, a geomagnetic sensor, an acceleration sensor, a wireless communication unit, a battery unit, and a sensor control unit. The walking sensing device is used to calculate the time at which the foot is on the ground by the negative slope of the gait pattern and analyzes walking symmetry according to a symmetry ratio of a walking pattern of a right foot and a left foot.

As shown by the above references, there exists a need to create better gait, balance, and stability analysis systems and methods.

One aspect of the disclosure is directed to a method for monitoring health parameters of an individual, including joint movements, gait, stability, balance, positional, and/or orientational changes to portions of a body. The method includes obtaining a plurality of measurements (e.g., relative position, position over time, etc.) of body portions over a period of time via a sensor system, transmitting the measurements from the sensor system to a mobile computing device, processing the measurements to track and analyze any change in the orientation, relative position, etc. of the body portions, and generating an alert output based, at least in part, on the analyzed change in orientation, relative position, etc. In some embodiments, processing the measurements (e.g., relative position, position over time, etc.) to track and analyze any change in movement, activity, etc. is performed fully or partially by the mobile computing device. In some embodiments, processing the measurements (e.g., relative position, position over time, etc.) to track and analyze any change is performed fully or partially by a network computing device that may receive the measurements (e.g., relative position, position over time, etc.) from the mobile computing device. In some embodiments, the method further includes querying the individual for user inputs. In such embodiments, the alert output may also be based, in part, on these user inputs. Additionally or alternatively, in some embodiments, the method also includes transmitting the measurements, user inputs, and/or other data acquired by the mobile computing device to a healthcare provider, coach, or other authorized user.

Another aspect of the disclosure is directed to a monitoring system configured to detect changes (e.g., orientation, relative position, position over time, etc.) to portions of a body. The monitoring system includes a sensor system wearable on or around portions of an individual's body, which is configured to obtain and transmit a plurality of measurements (e.g., relative position, orientation, position over time, etc.) of one or more body portions over a period of time. The monitoring system also includes a mobile computing device, which includes a processor and a non-transitory computer-readable medium with instructions stored thereon. The instructions, when executed by the processor, cause the processor to: receive the transmitted measurements (e.g., orientation, relative position, position over time, etc.), process the measurements to track and analyze any change in the body portions, and generate an alert output based, at least in part, on the analyzed change. In some embodiments, the instructions stored on the computer-readable medium further cause the processor to query the individual for user inputs. In such embodiments, the alert output may also be based, in part, on these user inputs.

Another aspect of the disclosure is directed to a monitoring system configured to detect bilateral joint movement or gait of a body. The monitoring system includes a sensor system wearable on or around one or more portions of an individual's body, which is configured to obtain and transmit a plurality of measurements (e.g., joint abduction, extension, flexion, joint movement, axis of joint movement, range of movement, acceleration, orientation, rotation, etc.) of one or more body portions over a period of time. The monitoring system also includes a mobile computing device, which includes a processor and a non-transitory computer-readable medium with instructions stored thereon. The instructions, when executed by the processor, cause the processor to: receive the transmitted joint movement and range measurements (e.g., joint abduction, extension, and flexion), process the joint movement and range measurements to track and analyze any change in joint health of the body portions, and generate an alert output based, at least in part, on the analyzed change in joint movement and range. In some embodiments, the instructions stored on the computer-readable medium further cause the processor to query the individual for user inputs. In such embodiments, the alert output may also be based, in part, on these user inputs.

In any of the embodiments described herein, the monitoring system is configured to monitor for common gait issues, or other medical conditions. In such embodiments, the monitored body portions may be, for example, the hips, chest, shoulders, knees, ankles, toes, head, elbows, wrists, and one or both legs. The body portion of some embodiments includes the head, including the ear, shoulders, chest, hips and the right and left legs of an individual, and the sensor system includes a first component configured to obtain a first plurality of balance measurements (symmetric heel strikes, symmetric toe offs from ground, rotation of legs, levelness of hip and/or shoulder, tilt of trunk, position of head and neck, and symmetric swinging of arms) over time from a fixed location on a first body portion, and a second component configured to obtain a second plurality of balance measurements over time from an equivalent fixed location on a second body portion. In some embodiments, there are 1 to 20 body portions measured; in other embodiments, there are 1 to 10, 10 to 20, 11 to 17, 15 to 17, 10 to 15, etc. body portions measured over time. In some such embodiments, processing the balance measurements to track and analyze any change in gait includes: comparing the first plurality of balance measurements to each other to detect a change in the movement of the first body portion over time, comparing the second plurality of movement measurements to each other to detect a change in the movement of the second body portion over time, and calculating a difference between the change in movement of the first body portion and the change in movement of the second body portion. The difference between the change in movement of the first body portion and the change in movement of the second body portion may contribute to a determination of a timing or content of the alert output. For example, the alert output may be generated when the difference between the change in movement of the first body portion and the change in movement of the second body portion exceeds a threshold value or displays a particular pattern (e.g., shoulder moves right to compensate for hip movement to the left).

In any of the embodiments described herein, the user inputs prompted and received by the mobile computing device include symptoms and/or risk factor data. Additionally or alternatively, the user inputs may include an indication of whether the individual has complied with a prescribed instruction. The prescribed instruction may be prescribed by a healthcare provider or the monitoring system. In some embodiments, the prescribed instructions are customizable by a healthcare provider via a remote computing device communicatively coupled to the mobile computing device.

In any of the embodiments described herein, the alert output includes an instruction to the individual to consult a healthcare provider for evaluation. In some embodiments, the alert output is generated when an overall score from a balance or gait assessment reaches or exceeds a predefined threshold or indicates a particular musculoskeletal health condition. The overall score from the balance or gait assessment may correspond to a likelihood of onset of or having a condition that causes changes in gait, stability, and/or balance. For example, the overall score of the balance or gait assessment may correspond to the likelihood that the individual has developed neuropathy or is recovering from a stroke or spinal injury. Various parameters may contribute to the overall score, including one or more of: symmetric heel strikes, symmetric toe offs from ground, rotation of legs, levelness of hip and/or shoulder, tilt of trunk, position of head and neck, symmetric swinging of arms, one or more user inputs related to symptoms or risk factors, etc.

In any of the sensorized embodiments described herein, the sensor system is configured to be coupled to any part of the body (i.e., any body portion) to measure sagittal, transverse, and/or coronal planar movements of the joints and measure acceleration, orientation, rotation, angular rate, flexion, extension, abduction, adduction, etc. For example, the sensor may be coupled to a magnetic mount (e.g., with a southpole of the magnet facing a skin surface of the user), which is coupled to the body portion using a disposable, dual-sided adhesive. Any of the sensor systems described herein are configured for continuous use for up to four months. Alternatively, other designs may be configured for hourly, daily, weekly, or monthly use. Any of the sensor systems described herein do not need to be re-charged, such that the built-in battery is optimized for use for the entire duration of the assessment. Alternatively, for other designs, re-charging may be needed, for example via wired connection or via contact charging. For example, in some embodiments, the sensor system described herein uses edge computing and algorithms embedded in the sensor system to detect body and joint movement while conserving battery life. Any of the sensor systems described herein may employ feedback (e.g., haptic, visual, auditory, etc.) to indicate to a user that an exercise or assessment has been performed adequately or correctly. The sensor design is contoured and asymmetrically weighted to prevent or reduce roll away and ensure roll towards a patient if the patient falls. For example, the sensor may not be a perfect circle which makes it hard to roll. Since the weight is not evenly distributed in the sensor, the sensor tilts immediately on rolling which causes it to fall before rolling too far. In some embodiments, one or more sensors described herein may be embedded, enclosed, or otherwise coupled to a soft plastic or silicone. In any of the embodiments described herein, the sensor system is configured to couple securely to the body portion. In any of the embodiments described herein, the sensor system may be coupled to, integrated into, or form part of a stretchable band, sleeve, belt, brace, or garment such as a sock, legging, or shirt.

Additionally, in some embodiments, for example to enhance movement detection, reflective markers (e.g., lines, dots, shapes, etc.) may be used to detect range of motion, orientation, and/or location of various body portions, for example the lower limb or limbs. The reflective markers may be detected using an image sensor (e.g., CCD or CMOS) in a mobile computing device or other computing device.

In some embodiments, the sensor system is further configured to detect one or more of: an orientation of the body portion, a movement of the body portion, an acceleration of the body portion, an angular rate of the body portion, a location of the body portion, etc. Such a sensor system may include one or more of: a gyroscope, an accelerometer, a magnetometer, and an image sensor, for example to measure movement of one or more body portions in nine degrees of freedom.

In some embodiments, a mobile computing device communicatively coupled to the sensor system or the sensor system itself is configured to generate an alert when the sensor system detects that gait, stability, and/or balance has changed. In some embodiments, the alert comprises a haptic alert. In some embodiments, a mobile computing device communicatively coupled to the sensor system or the sensor system itself is configured to generate outputs that include health-related feedback and/or recommendations based on one or more of the sensor readings.

Disclosed herein are devices, systems, and methods for monitoring one or more health parameters of an individual, including gait, stability, balance, and/or movement changes to one or more body portions. The devices, systems, and methods of various embodiments are additionally intended to track and increase compliance with health and wellness recommendations and improve health and wellness outcomes.

FIG. 1 illustrates one example of a health monitoring system configured to obtain, analyze, and respond to gait, stability, balance, and/or movement measurements of multiple body portions of an individual (e.g., symmetric heel strikes, symmetric toe offs from ground, rotation of legs, levelness of hip and/or shoulder, tilt of trunk, position of head and neck, symmetric swinging of arms, etc.). As illustrated, the monitoring system 100 includes a sensor system 110, and a mobile computing device 120, and optionally a server 130. The system 100 may additionally be configured to form a connected network in which physicians, coaches, and/or other authorized users can track the progress of the monitored individual and/or individualize instructions and feedback provided to the monitored individual.

In various embodiments, the sensor system 110 is configured to be worn by a subject. A subject who wears the sensor systems described herein may be interchangeably referred to as a user, patient, individual, person, or athlete. It will be appreciated by those skilled in the art that the subject monitored by the various devices and systems described herein may be any mammal or other animal.

The sensor system 110 comprises one, one or more, or a plurality of sensors coupled to various body portions. The sensor may be coupled or attached to a disposable adhesive, a stretchable component, and/or integrated into clothing, for example a strap, brace, belt, garment, shoe, sock, helmet, hearing aid, earbuds, shirt, pants, or other wearable material designed to be fitted around or coupled to a body portion. As used herein, the body portion may refer to one or both legs, one or both arms, a torso, a chest, a belly, a waist, a head, one or both shoulders, one or both hips, one or both knees, one or both sets of toes, forehead, head (e.g., top, side, back, etc.), one or both elbows, one or both wrists, and/or other body part. The sensor is configured to sense an amount, direction, orientation, rotation, acceleration, and/or range of motion in each body portion to analyze balance, stability, and/or gait. As used herein, the sensor module includes all sensors, power supply, signal processing electronics, controlling logic, and digital transmission devices needed to sense the amount, direction, and/or range of movement in each body portion, obtain the amount, direction, and/or range of movement in each body portion, and transmit the amount, direction, orientation, rotation, acceleration, and/or range of motion in each body portion to the mobile computing device 120. The sensor system may additionally include other sensors such as sensors configured to detect circumference, temperature, color, and/or any other biometric (e.g., pulse, blood oxygenation, impedance, etc.).

As used herein, the mobile computing device 120 refers to both the hardware and the application software of the computing device that communicates with the sensor system 110. The mobile computing device 120 is configured to receive, process, and analyze sensor data from the sensor system 110. It may be further configured to query an individual for user inputs, generate reminders, and other alerts to the individual, provide access to relevant health-related information, and generate and transmit messages intended for physicians, coaches, caregivers, or other authorized users of the system. In some embodiments, all or a portion of analysis of the sensor data is performed by the sensor system 110. For example, the mobile computing device 120 may perform initial data cleansing of outliers in the data as well as compute the joint-sensor model 810. Further, the mobile computing device 120 may be used to apply the posture master model 830 to choose between the joint-vision model and joint-sensor model. Similarly, the mobile computing system may apply the joint-vision model to recognize one or more body portions. Applying the joint-vision model to the incoming video (subsequently parsed into individual images or frames) saves a large amount of data being transmitted between computing device 120 and computing device 130. In some embodiments, computing device or server 130, learns or trains each of the machine learning models described elsewhere herein.

In some embodiments, the mobile computing device 120 is a smartphone, wearable computing device, notebook computer, laptop computer, tablet, or other portable computing device configured to pair with the sensor system 110. In other embodiments, the mobile computing device 120 may be any other personal computing device configured for wired or wireless connection to the sensor system 110.

The mobile computing device 120 further includes an image sensor (e.g., CCD, CMOS, etc.) configured to detect or locate specific body portions in an image or picture (e.g., 3D or 2D image or picture) of the user. The detected body portions are then processed by the processor on the mobile computing device 120 or a processor on another computing device to detect a location of one or more body portions and/or measure angles of joints, range of movement, orientation, etc. In some embodiments, reflective lines on clothing and/or reflective markers (e.g., dots or badges or shapes positioned on the patient) may be positioned on the various body portions to improve or enhance detection of the specific body portions in the image (e.g., 3D or 2D image). The analysis performed by the mobile computing device 120 may include analysis of a monitored individual's data and population-wide data. One or more aspects of the analysis or outputs of the analysis may also be configured for integration with electronic medical records.

Further, as shown in FIG. 1, the mobile computing device 120 is connected, at least at times, to the sensor system 110 via a communication link. In some embodiments, the mobile computing device 120 is wirelessly coupled to the sensor system 110 via a nearfield communications (NFC) protocol, a low energy Bluetooth® protocol, or other radiofrequency (RF) communication protocol. In some embodiments, the sensor system 110 is additionally or alternatively configured to communicate with the mobile computing device 120 via a databus and a wired (e.g., removable cable) connection. In some embodiments, communication between the sensor system 110 and the mobile computing device 120 is bidirectional; in other embodiments, communication is unidirectional with data pushed from the sensor system 110 to the mobile computing device 120.

In various embodiments, the mobile computing device 120 is coupled to the server 130 via a bidirectional communication link. In particular, the mobile computing device 120 may be connected to the server 130 via a CDMA, GSM, LTE, or other cellular network, via Wi-Fi®, or via any other suitable wireless or wired communication protocol.

The server 130 of some embodiments is a cloud-based server. It may be formed of one or multiple computing devices, including an application server, an internet server, a database server, or a combination thereof. In some embodiments, the server 130 is operated, managed, controlled, maintained, or owned by a system administrator. The server 130 refers to the hardware and software that contains and implements a backend of the system that stores all patient data. It also stores all instructions that are transmitted to and downloadable by the mobile computing device 120. These include application instructions (i.e., software) and data analysis instructions and methods.

Together, the components of the monitoring system 100 function to execute various algorithms and perform various methods, including obtaining, analyzing, and responding to movement, range of motion, balance, stability, and/or gait measurements of a body portion.

Figure 2:
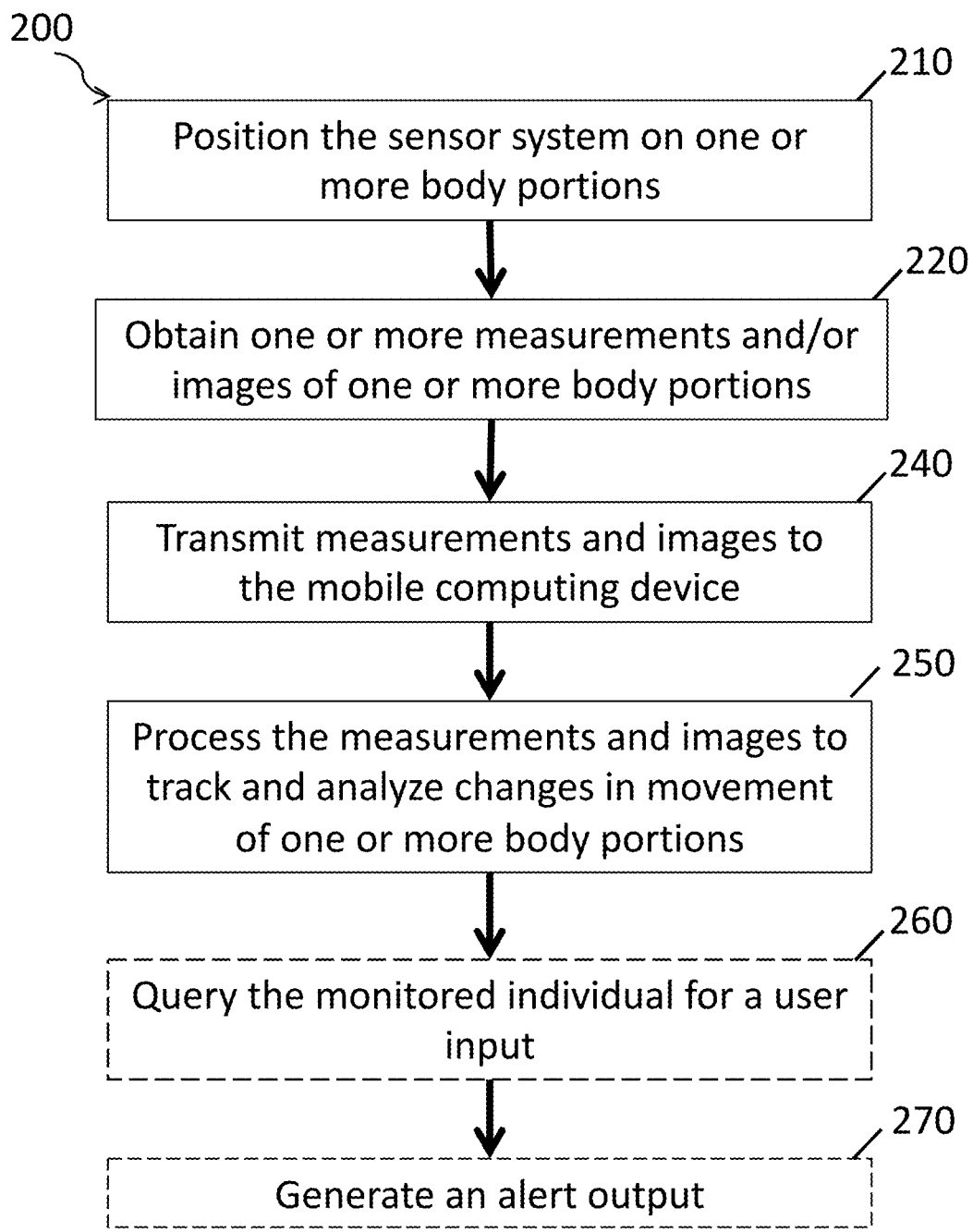
FIG. 2 illustrates a flow chart of one embodiment of a method of using the monitoring system of FIG. 1.

FIG. 2 depicts one example of a method 200 of using the monitoring system 100 described above. As shown at block 210, the method includes positioning the sensor system 110 on one or more body portions. The sensor system 110 may be secured to or around the plurality of body portions by the monitored individual or with the help of a physician, athletic trainer, other supervisor, friend, family, caregiver, or other reviewer. The sensor system 110 of some embodiments is usable for an extended time frame (e.g., one to five months), reusable, and configured to permit repeated attachment to and detachment from the body portion. In some embodiments, the sensor system 110 is shaped to conform to one or more contours of the individual's body or is otherwise configured so as to facilitate accurate positioning of the sensor system 110 at the same location each time it is worn. Each sensor of the sensor system 110 includes an identification tag. Upon placement of each sensor on a body portion of a patient, the mobile computing device is configured to communicatively (e.g., via Bluetooth, low-energy Bluetooth, near-field communication, or other radiofrequency or wireless signal) couple to the sensor and either manually (through user input) or automatically detect to which body portion the sensor is coupled. As such, as the sensor measures various movements of the body portion, the movements will be correlated or connected to a body portion.

As shown at block 220, the method 200 further includes obtaining one or more measurements (e.g., using one or more sensors) and images (e.g., using one or more imaging sensors, either with 2D or 3D image capture), of the one or more body portions via the sensor system 110, including, for example, a movement, direction of movement, orientation, acceleration, rotation, angular rate, and/or range of motion measurements (e.g., orientation, acceleration, symmetric heel strikes, symmetric toe offs from ground, rotation of legs, levelness of hip and/or shoulder, tilt of trunk, position of head and neck, symmetric swinging of arms). In some embodiments, one or more images of the one or more body portions are obtained via an image sensor (e.g., capturing 2D or 3D images) in a mobile computing device or image-capture device. As described in more detail in the next section, in some embodiments, obtaining the one or more measurements and images includes: sensing a change in movement indicative of and/or correlated to a change in balance, stability, and/or gait; and calculating, for example using one or more machine learning models described elsewhere herein, a balance, stability, and/or gait of the monitored individual from the sensed movement or a change in the sensed movement. In some embodiments, the movement is sensed overtime, such that some measured times may show normal or near normal stability, balance, and/or gait while other measured times may show abnormal stability, balance, and/or gait. In some embodiments, obtaining the one or more measurements further includes obtaining a baseline. A baseline measurement may comprise the patient performing a predetermined movement or exercise or standing still (not moving) to enable the sensor system or an image sensor to achieve a baseline reading or image (e.g., either in 2D or 3D). The calculated balance, stability, and/or gait may be a relative measurement (i.e., a measure of change from the baseline or from a previous measurement). In some embodiments, obtaining a plurality of measurements of the body portion further includes obtaining measurements (e.g., absolute or relative measurements) of one or more additional health-related parameters. For example, in some embodiments, the sensor system 110 is configured to obtain measurements indicative of one or more of a change in: circumference of the body portion, color of the body portion, temperature of the body portion, pulse, heart rate, blood oxygenation (i.e., pulse oximetry), blood volume (i.e., plethysmography), and/or other health parameters.

The method 200 also involves transmitting the measurements from the sensor system 110 and/or an image sensor to a communicatively coupled mobile computing device 120 or other computing device, as shown at block 230. The transmitted measurements may include any obtained by the sensor system 110 and/or image sensor, including, for example, movement, range of motion, orientation, acceleration, direction of movement, angle of movement, etc., or a combination thereof. The mobile computing device 120 may integrate the sensor system measurements and one or more images acquired with the image sensor to further assess or measure balance, stability, and/or gait, as described elsewhere herein.

At block 240, the measurements and/or images are processed to track and analyze changes or disparities in movements of one or more body portions. In some embodiments, balance, stability, and/or gait measurements are tracked over time and changes are analyzed, for example, to determine when the balance, stability, and/or gait change has exceeded a predefined threshold value or whether balance or gait has changed from a previous measurement. Similarly, any other parameters being measured may be tracked over time and analyzed. In some embodiments, each measured parameter contributes to an overall balance, stability, or gait score, and analyzing the measurements involves weighting the changes in each parameter or movement of each measured body portion, calculating an overall score, and determining if the overall score has exceeded a predefined threshold value. In some embodiments, processing the measurements to track and analyze changes is performed partially or fully by the mobile computing device 120. Additionally or alternatively, in some embodiments, some of or all the processing, tracking, and analysis is performed on the sensor system 110.

Optionally, in some embodiments, the method 200 further includes querying the individual for user inputs, as shown at block 250. Such queries are presented to a physician or monitored individual on the mobile computing device 120. The requested user inputs may vary depending on the intended use of the monitoring system 100. For example, the mobile computing device 120 may prompt a user to enter one or more of: biographical information, the patient's current weight, medical history, current symptoms, risk factor data, a pregnancy status (e.g., a gestation age, conception date, or due date), an exercise performed, a food consumed, a supplement consumed, a medication administered, a duration of sleep attained, a daily wellness rating, a location of pain or discomfort, and an indication of whether the monitored individual has complied with a prescribed instruction.

The monitoring system 100 optionally generates an alert output at block 260. The alert output may be a visual, tactile, and/or audio output generated by the mobile computing device 120. The alert output may provide a warning, recommendation, positive feedback, progress alert, or any other useful message. The alert output is based, at least in part, on the measured balance, stability, and/or gait or an analyzed change in balance, stability, and/or gait. For example, the alert output may be generated by the mobile computing device 120 upon detecting that the gait is outside of a "normal" or "healthy" range or that the gait change exceeded a predefined threshold or changed from a previous measurement. In other embodiments, the alert output is generated by the mobile computing device 120 at a regular time interval, and the information conveyed in the alert output varies depending on the body portion's movement, direction of movement, range of motion, orientation, angular rate, acceleration, etc. or a combination thereof or a change in one or more parameters. In some embodiments, the alert output may also be based, in part, on the analysis of other parameters being measured and/or the user inputs.

Figure 3:
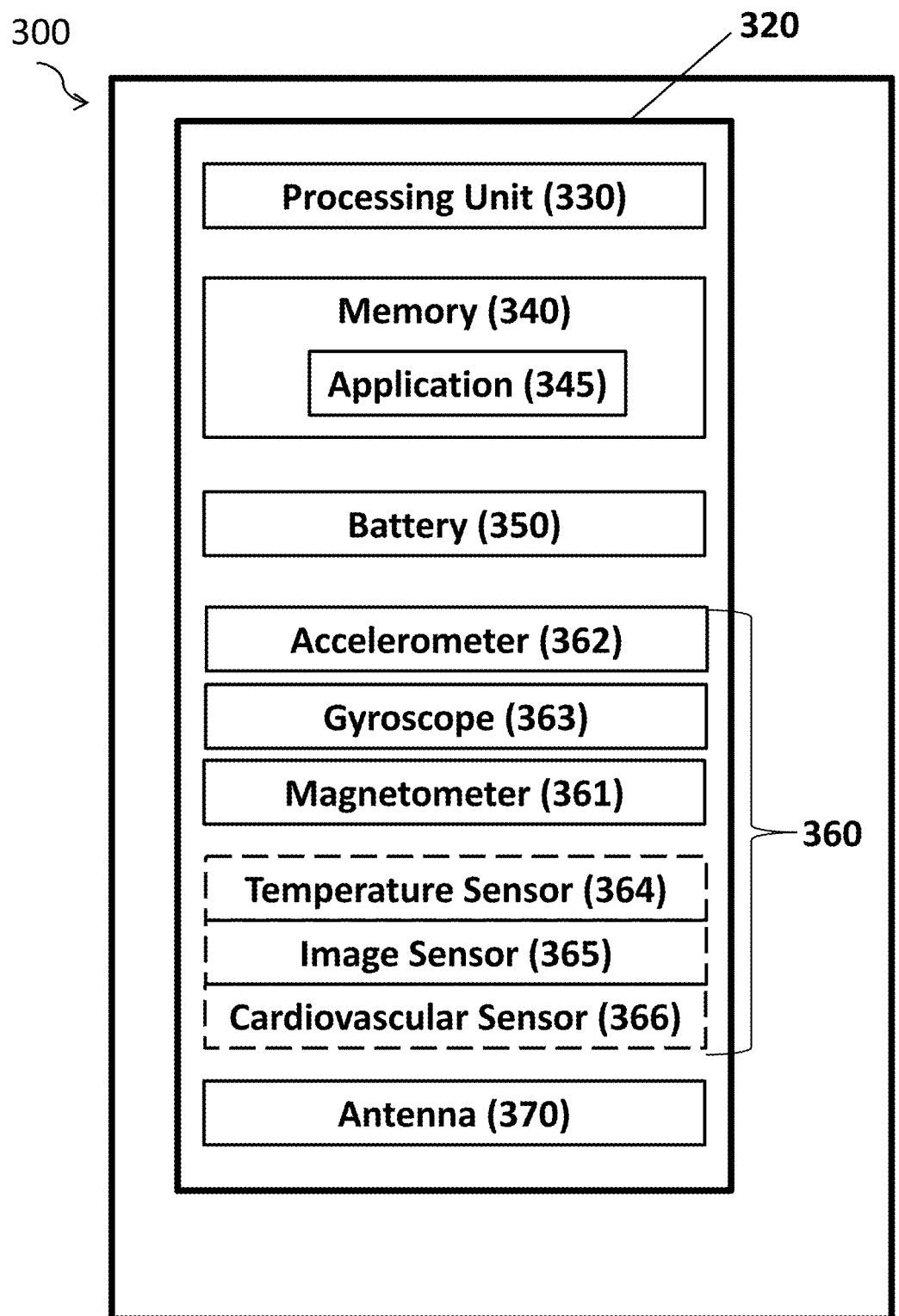
FIG. 3 illustrates a functional block diagram of one embodiment of a sensor system provided within the monitoring system of FIG. 1.

A functional block diagram of one embodiment of a sensor system is provided in FIG. 3. While numbered uniquely, one skilled in the art will appreciate that the sensor system 110 of FIG. 1 may be formed of any embodiment of a sensor system described herein and may include any of or all the functional components described with respect to the sensor system 300 shown in FIG. 3. Moreover, although illustrated separately, it is to be appreciated that the various functional blocks of the sensor system 300 need not be separate structural elements.

The sensor system 300 of various embodiments includes a coupling component 310 (e.g., adhesive) configured to fit securely to a body portion, and a sensor module 320 coupled thereto. In some embodiments, at least a portion of the sensor module 320 is removable from the coupling component 310. For example, the coupling component 310 may be formed of a machine-washable fabric, a soft plastic, or silicone, and at least a portion of the sensor module 320 may be housed, embedded, encased, or otherwise coupled to the coupling component 310. In some embodiments, a first portion of the sensor module 320 is integrated into the coupling component 310 while a second portion extends from or is separate from the coupling component 310. For example, a processing unit 330 and a battery 350 may also form part of the sensor module 320.

As shown in FIG. 3, the sensor module 320 includes a processing unit 330, which may be a general purpose microprocessor, a digital signal processor (DSP), a field programmable gate array (FPGA), an application specific integrated circuit (ASIC), or other programmable logic device, or other discrete computer-executable components designed to perform the algorithms and functions described herein. The processing unit 330 may also be formed of a combination of computing devices, for example, a DSP and a microprocessor, a plurality of microprocessors, one or more microprocessors in conjunction with a DSP core, or any other suitable configuration.

In various embodiments, the processing unit 330 is coupled, via one or more buses, to the memory 340 in order for the processing unit 330 to read information from and write information to the memory 340. The processing unit 330 may additionally or alternatively contain memory 340. The memory 340 can include, for example, processor cache. The memory 340 may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include application software 345 stored in a non-transitory format. The software, when executed by the processing unit 330, causes the processing unit 330 to perform one or more operations described elsewhere herein.

In various embodiments, a power supply, such as a battery 350, is electrically coupled to provide power to the processing unit 330 and other electronic components. The battery 350 may be rechargeable or disposable. Additionally, some embodiments of the sensor module 320 may include one or more signal processing components, such as a filter (e.g., low pass, high pass, or band pass filter), an amplifier, and/or an analog-to-digital (AD) converter.

As shown, the sensor module 320 includes one or more sensors 360 configured to detect parameters indicative of the monitored individual's health. In some embodiments, the sensor module 320 additionally includes one or more of: an accelerometer 362, a gyroscope 363, a magnetometer 361, a temperature sensor 364, an image sensor 365, and/or one or more cardiovascular sensors 366. The accelerometer 362, gyroscope 363, and magnetometer 361 together operate (as an inertial measurement unit or IMU) to measure 9 degrees-of-freedom (9 DOF) or force, angular rate, and orientation of a body portion. The accelerometer 362 measures acceleration or orientation along the x, y, and z axes. The gyroscope 363 measures rotation or angular rate along the x, y, and z axes. The magnetometer 361 measures force in the x, y, and z axes. The x, y, and z axes are defined with respect to the body of the sensor. The optional temperature sensor 364 of some embodiments is a thermistor, thermometer, or other temperature-responsive sensor configured to detect changes in skin temperature at the body portion. The one or more cardiovascular sensors 366 may include, for example, a pulse oximeter, a plethysmograph sensor, a pulse rate monitor, and/or a heart rate monitor. The image sensor 365 of some embodiments is a camera (e.g., may or may not include three-dimensional or depth information), semiconductor charge-coupled device (CCD), or complementary metal-oxide-semiconductor (CMOS) configured to detect changes in the attenuation of light waves indicative of changes in skin color at the body portion. Additionally or alternatively, the image sensor 365 is included in the mobile computing device and configured to capture one or more images (e.g., 2D or 3D) of one or more body portions to assess, at least in part, balance, stability, and/or gait of the user.

In various embodiments, some of or all the measurements obtained by the sensor system 300 are transmitted wirelessly, for example, via a communication antenna 370, to the mobile computing device 120 for processing, analysis, and/or storage. The communication antenna 370 may be, for example, a transmitter or a transceiver. The measurements may be automatically pushed to the mobile computing device 120 or retrievable by a request from the mobile computing device 120. In some embodiments, the measurements from the sensor system are transmitted at a fixed rate, for example one reading per second or 250 readings per second. The transmission rate of sensor readings may be 1 to 100 readings per second, 100 to 500 readings per second, 500 to 1,000 readings per minute, 100 to 1,000 readings per minute, 1,000 to 10,000 readings per minute, etc. Alternatively, the measurements from the sensor system are transmitted at a variable rate and/or on-demand.

Figure 4A:
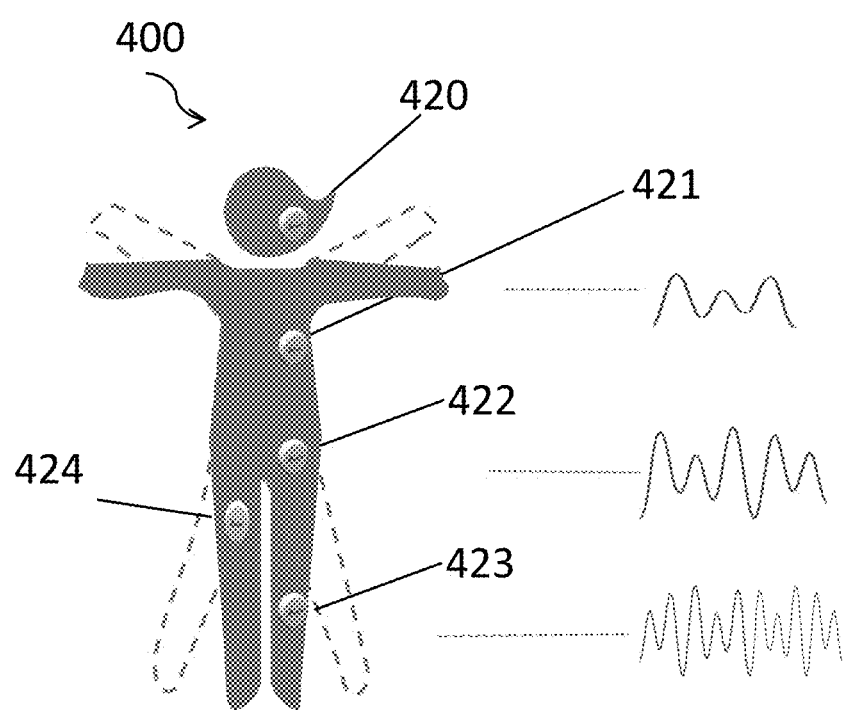
FIGS. 4A-4B illustrate exemplary, non-limiting positioning of various sensors of the sensor system to measure balance, stability, and/or gait.
Figure 4B:
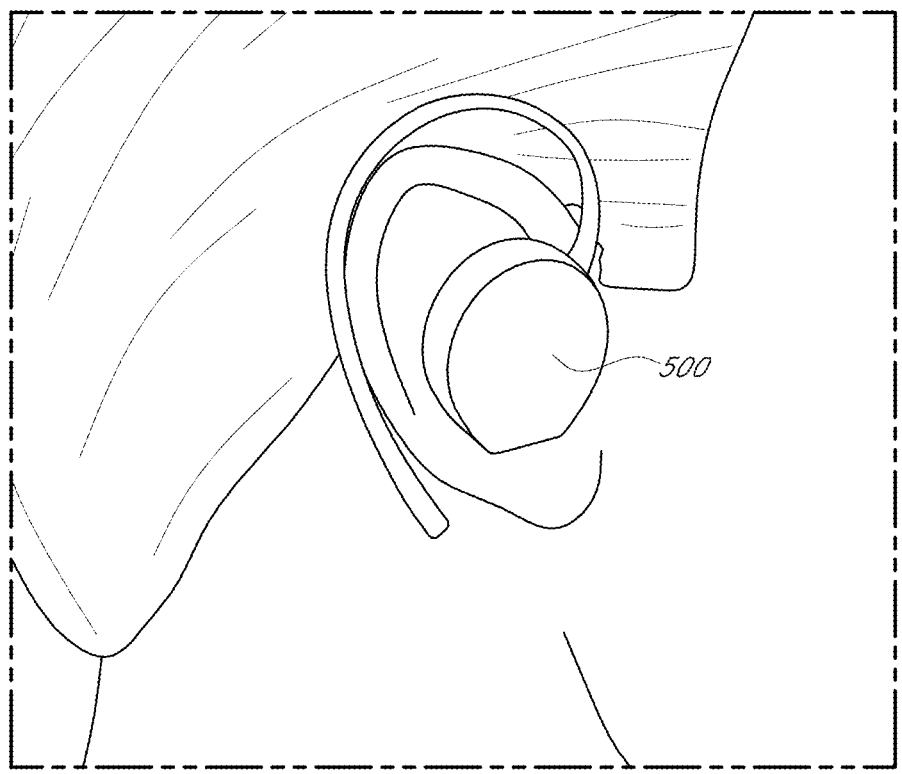

Various, non-limiting embodiments of the sensor system 300 are provided in FIGS. 4A-4B. As shown in FIG. 4A, each sensor system 400 includes one or more sensors positioned around the body to measure movement 420, 421, 422, 423, 424. Sensors 420, 421, 422, 423, 424 allow for the measurement of movement of various body portions. For example, the sensor system 400 may measure orientation, rotation, angular rate, or acceleration of a body portion, force exerted by a body portion, a symmetry of heel strikes, a symmetry of toe offs from ground, a rotation of each leg (internal and external), a levelness of each hip, a levelness of each shoulder, a side tilt of trunk (left and right), a rotation of trunk, a position of head and neck, and a symmetry of arm swing. The combination of some or all of these measurements determines joint health, gait, stability, and/or balance. In some embodiments, the sensor system 300 is formed of a strap, band, or belt. The entirety of the strap, band, or belt may be deformable and circumferentially stretchable, or only a portion of it may be configured to stretch. The strap, band, or belt may be sized and configured for placement on an upper torso or chest or lower torso or waist. Alternatively, it may be sized and configured for placement on a limb, such as an upper arm, lower arm, upper leg, and/or lower leg.

In some embodiments, as shown in FIG. 4B, one or more sensors are positioned on, in, or proximate to an ear of the user using, for example, a magnetized ear clip or adhesive. For example, FIG. 4B depicts one example of an inner ear sensor module 500. The inner ear sensor module 500 may be integrated into earbuds, hearing aids, headphones, hearing protection devices, or the like. Positioning of sensor module 500 on, in, or proximate to an ear of the user allows the sensor system to accurately measure head, neck, and/or upper body or cervical movements and orientation. The importance of such measurements will be described elsewhere herein.

Figure 5A:
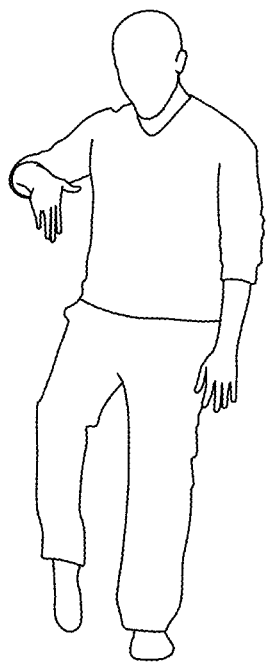
FIGS. 5A-5I illustrate various, non-limiting gaits that are measurable by the systems and methods described herein.

In some embodiments, the sensor system 400 is used to monitor for various types of gait. Various, non-limiting types of gait will now be described in turn with reference to FIGS. 5A-5I. Although various, exemplary gaits are shown, one of skill in the art will appreciate that the systems and methods described herein can be applied to assess or measure any type of movement or gait. FIG. 5A shows an embodiment of slap gait as an indicator of muscle weakness or neuropathy. Slap gait occurs when there is muscle weakness in one leg, for example the right leg, so that the right foot slaps on the floor while walking and can cause a fall by the patient. In such an embodiment, sensor system 400 measures an asymmetrical impact force on the right foot together with image-based sensing through computer vision to measure gait.

Figure 5B:
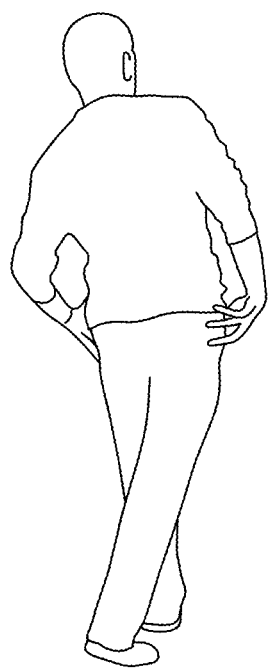

In some embodiments, the sensor system 400 is used to identify Trendelenburg gait, as shown in FIG. 5B. Trendelenburg gait occurs when the hips are not horizontal while walking with the shoulders leaning at a tilt. Trendelenburg gait is caused by weakness in the abductor muscles of the lower limb, gluteus medius, and/or gluteus minimus. Trendelenburg gait can be indicative of neuronal injury, muscular dystrophy, hemiplegic cerebral palsy, and is often seen in patients after hip replacement surgery. In some instances, gait is observed from both right and left sides; in other instances, gait is observed from either the right side or left side. In such embodiments, sensor system 400 measures movement of both hips, both shoulders, and movement of both feet to detect Trendelenburg gait. For example, a first set of sensors or a first sensor measures asymmetrical hip movement or positioning (i.e., hip tilt) in a first direction, a second set of sensors or a second sensor measures asymmetrical shoulder movement or positioning (i.e., shoulder tilt) in a second direction opposite the first direction, and a third set of sensors or a third sensor measures movement of both feet. Alternatively to the third set of sensors or any of the preceding sensors, computer vision using an image sensor measures foot movement correlated in time with the measurements sensed by the first and second sensors (i.e., hip and shoulder movement, respectively), as described elsewhere herein.

Figure 5C:
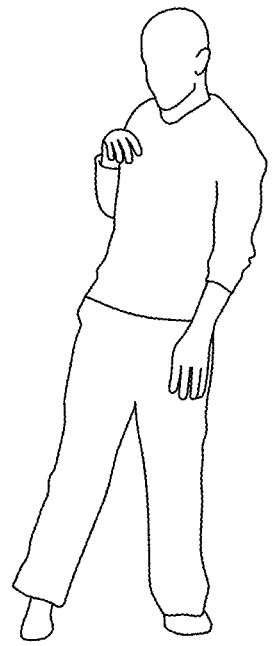

In some embodiments, the sensor system 400 is used to identify hemiplegic gait, for example following stroke, as shown in FIG. 5C. Hemiplegic gait involves one leg without normal flexion potential at the hip causing distance between the two legs to rise and fall, with the elbow bent for balance. The sensor system 400 may use computer vision image-based sensing, for example with an image sensor, to measure the distance between the legs. Additionally, sensor system 400 may identify the bent elbow and/or circular movement of the foot.

Figure 5D:
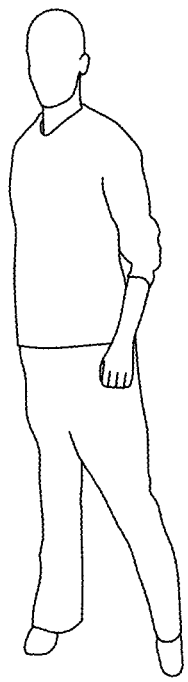

In some embodiments, the sensor system 400 is used to identify diplegic gait, for example, associated with spinal injury, as shown in FIG. 5D. Patients have involvement with both lower limbs with both legs moving in a circular motion having heels raised. Sensor system 400 may use computer vision imaging to identify toe raise height and arc of back, with an additional sensor to measure impact force of steps.

Figure 5E:
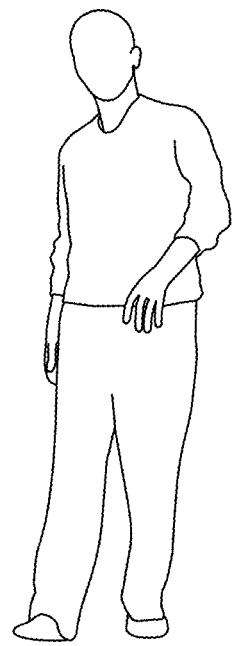

In some embodiments, the sensor system 400 is used to identify antalgic gait associated with pain compensation, as shown in FIG. 5E. The body has normal swing on the unaffected side, with abnormal shorter swing steps on the affected side. Sensor system 400 is configured to determine an absolute time between impacts on the left and right side to identify which side is taking shorter steps. Further, computer vision imaging, for example using an image sensor, may be used to identify asymmetry between the left and right sides.

Figure 5F:
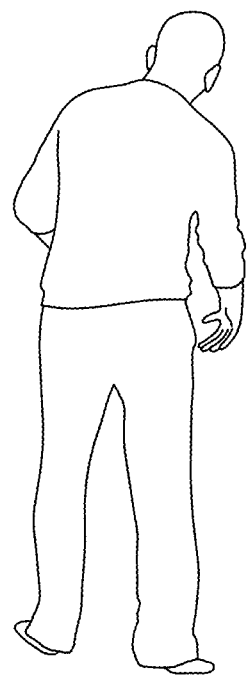

In some embodiments, sensor system 400 is configured to identify an ataxic wide based gait, as shown in FIG. 5F. Patients experiencing ataxic wide based gait are unsteady and staggered, almost falling before pulling back. Ataxic wide based gait may result from neurological abnormalities, pain, or muscle abnormalities in the hips, legs, or feet. Sensor system 400 is configured to determine body movement while walking, and a computing device is configured to use computer vision imaging, using for example an image sensor, to identify a width of gait.

Figure 5G:
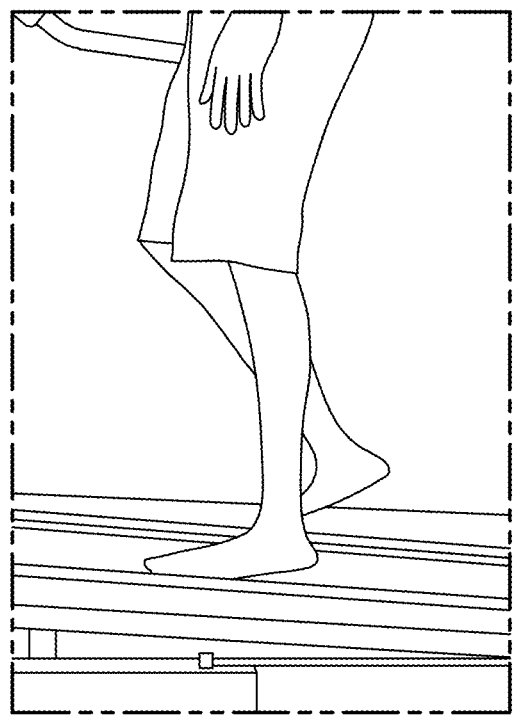
Figure 5H:
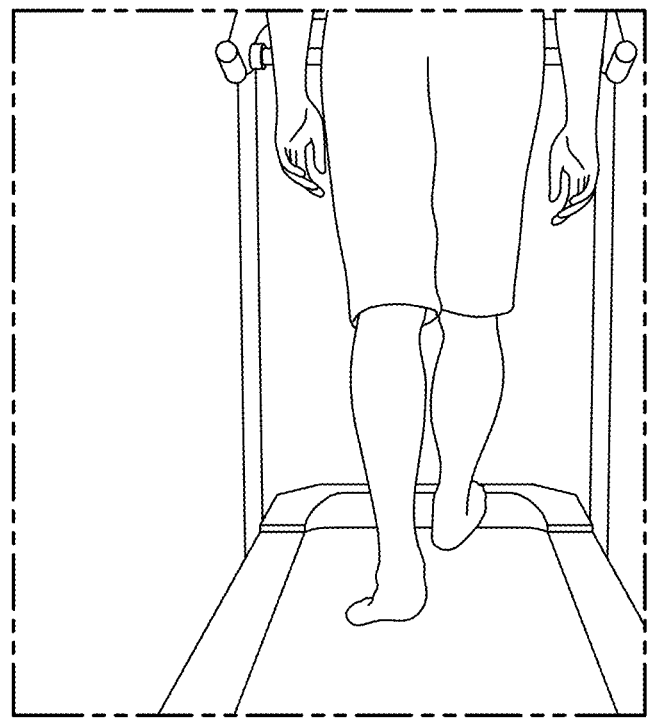

In some embodiments, sensor system 400 is configured to identify inefficient gait stance where one heel starts raising before the other heel has not passed the center of gravity and may be indicative of neurological damage, as shown in FIGS. 5G-5H. Sensor system 400 is configured to determine movement, especially movement in three dimensions and/or slow movements. A computing device is configured to use computer vision imaging, using for example an imaging sensor, to determine movement, especially heel movement, while walking, and other movements in two dimensions, as described in further detail elsewhere herein. Sensor system 400 may also be positioned on both legs to identify early lift while walking, as shown in FIG. 5H.

Figure 5I:
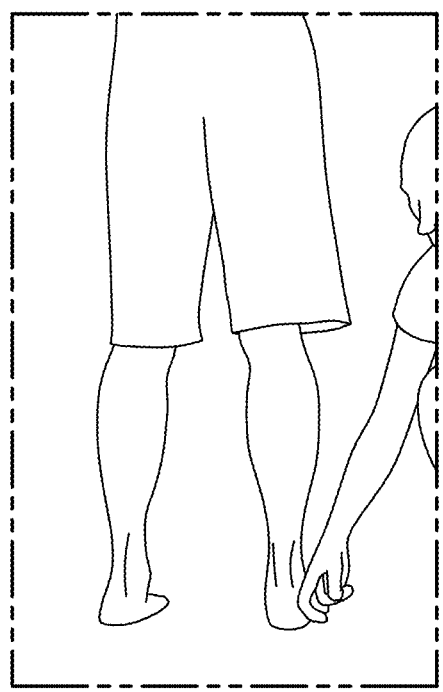

In some embodiments, the sensor system 400, for example an image sensor, is configured to identify heel eversion while the feet are on the ground, as shown in FIG. 5I. Heel eversion occurs when the Achilles tendon is concave as demonstrated by the curved finger next to the foot in FIG. 5I and can result in the foot rolling in with the heel everting following the placement of weight on the leg. Historically, it has been difficult to calculate precise measurements in eversion. The computing device is configured to use computer vision imaging, for example using an imaging sensor, to mark an exact outline of the foot down to 1 to 2 pixels and can monitor and measure the eversion over time as measurements of pixels.

Further, in any of the embodiments described elsewhere herein, sensor system 400 and/or computing device may be used to detect movement through the use of computer vision imaging, for example using an image sensor, to detect range of motion, the angle of joints observed on the limbs, location of various body portions, etc.

In various embodiments, the sensor system 300 is removable and configured for repeated reattachment. In order to achieve consistent, reliable, and accurate results, it is desirable for the various sensors to be located at the same locations with each reattachment. To facilitate proper positioning of the sensors, in some embodiments, the sensor system 300 is integrated into clothing or a brace. For example, one or more coupling components 310 and sensor modules 320 may be integrated into a shirt, sports bra, shorts, leggings or pants, underwear, compression socks or other socks, partial socks or sleeves, knee brace, ankle brace, or any other suitable garment. In some embodiments, reflective markers (e.g., stripes, dots, etc.) may be coupled to or integrated into a clothing article to monitor and assess movement.

In some embodiments, including any of the embodiments described herein, at least a portion of the sensor module 320 is removable. The removable portion of the sensor module 320 may be securable to the coupling component 310 via any suitable attachment mechanism. For example, the coupling component 310 may include a cradle or holder sized to receive the removable portion of the sensor module 320, and the removable portion of the sensor module 320 may snap or clip into the holder. Alternatively, the removable portion of the sensor module 320 may zip or hook into place, or it may slide between layers or into a pocket of the coupling component 310. In some such embodiments, the coupling component 310 is washable. In some embodiments, the removable portion of the sensor module 320 is enclosed in a water-resistant or water-proof protective casing. In some embodiments, the removable portion of the sensor module 320 may house the processing unit 330 and any associated electrical filtering and processing components, the battery 350, an accelerometer, a gyroscope, a magnetometer, and/or one or more additional parameter sensors. In some embodiments, the removable portion is interchangeable and configured for attachment to a plurality of garments and devices. In some embodiments, the removable portion is automatically activated upon attachment to a garment or automatically deactivated upon detachment from a garment.

Figure 6:
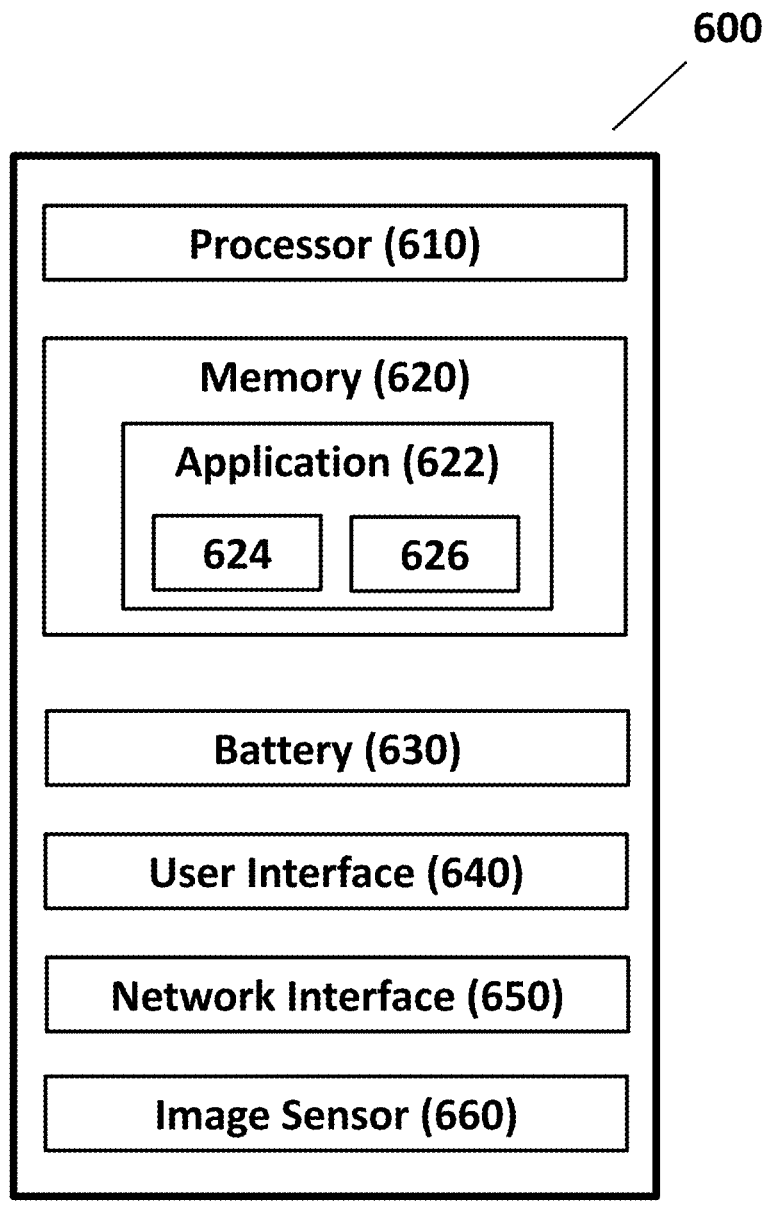
FIG. 6 illustrates a functional block diagram of one embodiment of a mobile computing device provided within the system of FIG. 1.

FIG. 6 provides a functional block diagram of one embodiment of the mobile computing device. While numbered uniquely, one skilled in the art will appreciate that the mobile computing device 120 of the system 100 may be formed of any embodiment of a mobile computing device described herein and may include any of or all the functional components described with respect to the mobile computing device 600 of FIG. 6. Moreover, although illustrated separately, it is to be appreciated that the various functional blocks of the mobile computing device 600 need not be separate structural elements.

The mobile computing device 600 of various embodiments includes a processor 610, for example, a general-purpose microprocessor. The processor 610 is coupled, via one or more buses, to the memory 620 in order to read information from and write information to the memory 620. The memory 620 may be any suitable computer-readable medium that stores computer-readable instructions for execution by computer-executable components. In various embodiments, the computer-readable instructions include software stored in a non-transitory format, some such software having been downloaded as an application 622 onto the memory 620. The processor 610, in conjunction with the software stored in the memory 620, executes an operating system and the application 622. Some methods described elsewhere herein may be programmed as software instructions contained within the application 622 stored in the memory 620 and executable by the processor 610.

In various embodiments, a power supply, such as a battery 630 is included within the mobile computing device 600 and is electrically coupled to provide power to the processor 610 and other electronic components. The battery 630 may be rechargeable or disposable.

The mobile computing device 600 of various embodiments includes a plurality of interfaces, such as a user interface 640 and a wireless network interface 650. The user interface 640 may include one or more input/output (I/O) devices. In some embodiments, the user input device includes one or more of a button, switch, touchscreen, and keyboard, and the output device includes one or more of a display screen, light display, audio output, and haptic output. The wireless network interface 650 of some embodiments includes a receiver and transmitter for bi-directional communication. The receiver receives and demodulates data received over a communication network. The transmitter prepares data according to one or more network standards and transmits data over a communication network. A communication antenna in the form of a transceiver may act as both a receiver and a transmitter. In some embodiments, the mobile computing device 600 includes a plurality of network interfaces 650, including a first network interface configured for communication with the sensor system 300 and a second network interface configured for communication with a server 130.

In various embodiments, a health monitoring application 622 is downloaded from a server 130 onto the mobile computing device 600 by the monitored individual. The health monitoring application 622 may include one or more of a user interaction module 624 and a data processing module 626.

The user interaction module 624 of various embodiments instructs the mobile computing device 600 to request information from, and provide information to, the monitored individual or user of the system (e.g., physician, healthcare professional, etc.). The user interaction module 624 includes a graphical user interface displayable on a screen through which the monitored individual can interact with the monitoring system. The monitored individual may also interact with the user interaction module 624 through audio and/or verbal inputs and outputs. For example, in some embodiments, the user interaction module 624 generates sounds through which the monitoring system can provide instructions and/or information to a monitored individual and query the monitored individual for information. In some embodiments, voice recognition capabilities allow a monitored individual to verbally respond to requests for information.

Figure 7:
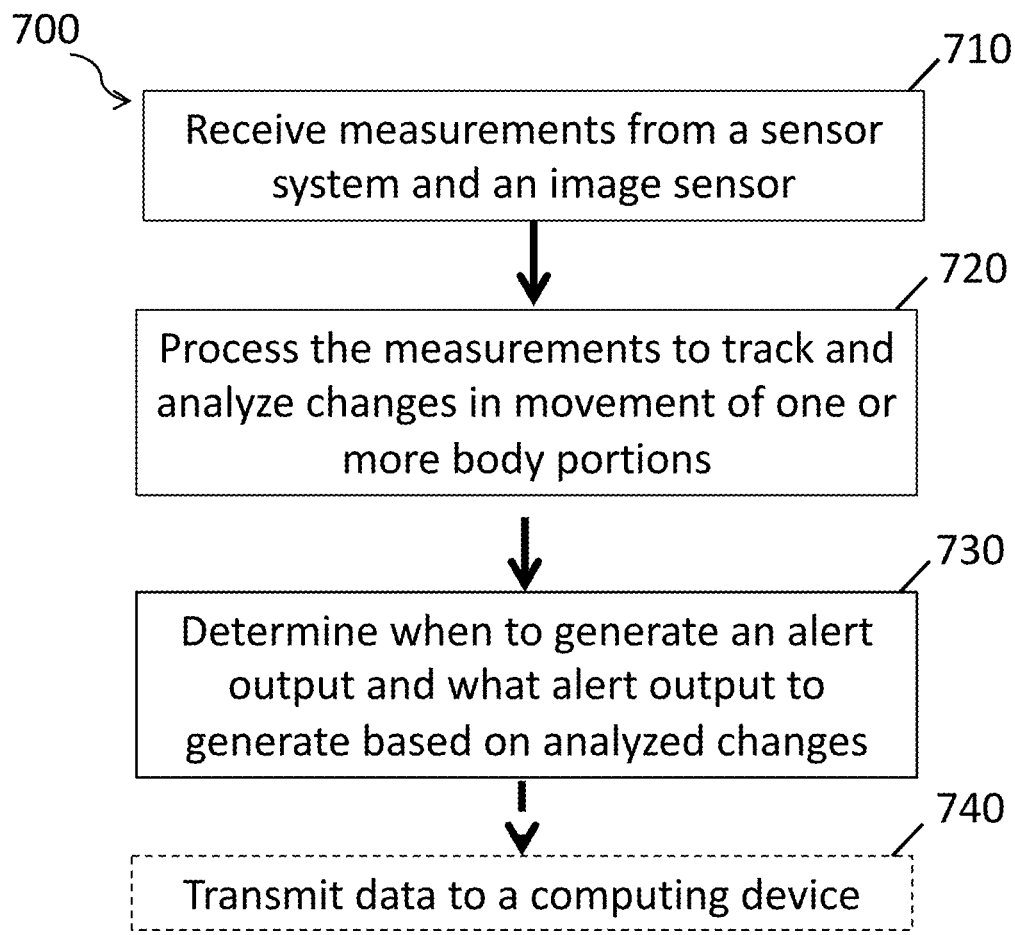
FIG. 7 illustrates a flow chart of one embodiment of a method performed by the sensor system of FIGS. 4A-4B or the mobile computing device of FIG. 6.

The health application 622 of various embodiments also includes a data processing module 626. The data processing module 626 includes the software that instructs the mobile computing device 600 to perform various data processing methods. One method directed by the software of the data processing module 626 is depicted in FIG. 7. As shown at block 710 of the depicted method, the mobile computing device 600 receives measurements from the sensor system 300 and/or image sensor 660. As described above, these measurements may be relative or absolute measurements acquired by the sensor system and/or an image sensor. The measurements include movement, acceleration, orientation, angular rate, stability, gait, etc. or any combination thereof. In some embodiments, the raw measurements are received by the mobile computing device 600 from the sensor system 300 and processed by the mobile computing device 600 to determine how one or more body portions moved. The mobile computing device 600 may also process data from image sensor 660 to determine how one or more body portions moved. Additionally, the measurements may optionally include one or more additional measurements of health parameters such as circumference, skin temperature, skin color, and/or cardiovascular performance (e.g., blood oxygenation, blood volume, pulse rate, or heart rate). At block 720, with the aid of the data processing module 626, the mobile computing device 600 processes the received measurements to track and analyze changes in movement of one or more body portions. Additionally, the mobile computing device 600 determines when to generate an alert output and what alert output to generate based on any measurement movement and/or analyzed changes in movement of the body portion, as shown at block 730. In some embodiments, the mobile computing device also optionally transmits data, including the received measurements, the analysis of measurements, and data received via user inputs to a computing device, for example a server, as shown at block 740.

In some embodiments, processing the received measurements to track and analyze changes in the body portions involves assigning a relative weight to one or more measured parameters of importance and calculating an overall score from the weighted measurements. The overall score may be an overall risk score, an overall balance score, an overall stability score, an overall gait score, or wellness score. In some embodiments, the overall score corresponds to an indication of a degree of abnormality of a measured gait, balance, stability, and/or joint movement or a likelihood of onset of a condition or a likelihood of having a condition. For example, the overall score may correspond to the likelihood that the monitored individual has developed neuropathy, muscle weakness, history of stroke, or any other injury that causes abnormal gait, balance, stability, and/or joint movement. In some embodiments, the overall score may correspond to the likelihood that the monitored individual may require hip surgery, spinal injury, knee surgery, and/or another type of surgery. As another example, the overall score may correspond to a monitored individual's level of success in improving overall wellness, balance, stability, or gait. One, some, or all of the measured parameters may contribute to the overall score, including one or more of: an orientation of one or more body portions, an acceleration of one or more body portions, an angular rate of one or more body portions, a movement of one or more body portions, etc.

In some embodiments, processing the received measurements to track and analyze changes in movement of the body portions involves using one or more machine learning algorithms, separately or in tandem, to determine movement, posture, gait, stability, and/or balance, as described elsewhere herein.

Additionally, in some embodiments, the specific data analysis functions performed by the mobile computing device 600 may be further customizable for each monitored individual. In some embodiments, the analysis functions stored in software of the data processing module 626 are modifiable by system administrators and/or health and wellness professionals via interaction with an analytics system stored on a network computing device.

Figure 8:
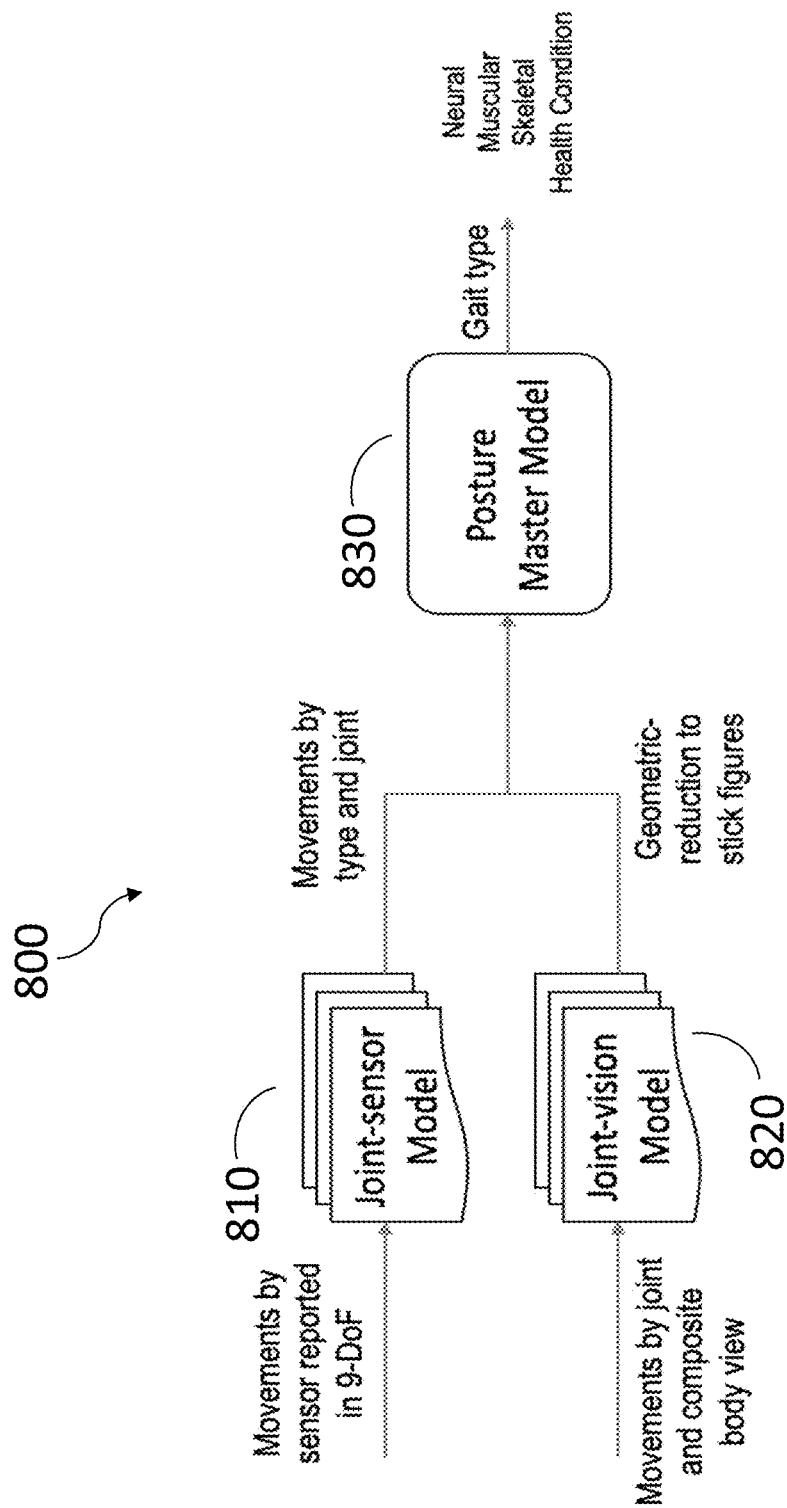
FIG. 8 illustrates a schematic block diagram of an analytics system for monitoring gait, stability, and/or balance.

FIGS. 8-16B show various aspects of the analytics system. The analytics may be performed wholly by the sensor system or the mobile computing device or another computing device or a combination thereof. In one embodiment, the analytics are performed by a mobile computing device communicatively coupled to the sensor system. Movement analysis and detection is performed by the analytics system by modeling data from human motion using data from a plurality of body sensors and computer vision. As shown in FIG. 8, the analytics system 800 comprises one or more machine learning models: a first machine learning model or a joint-sensor model 810, a second machine learning model or a joint-vision model 820, and a third machine learning model or a posture-master model 830. The machine learning models may be used in tandem or simultaneously, such that the output data is used collectively to determine a gait, balance, movement, etc. of the user, or alternatively depending on accuracy of the model for the given data set and/or user movement. Each model may also be used in isolation to output a movement of a user. For example, user movement may be acquired and analyzed by a joint-sensor model alone. Further for example, user movement may be acquired and analyzed by a joint-vision model alone. Still further for example, user movement may be acquired and analyzed by a posture-master model alone.

The joint-sensor model 810 uses one or more sensors positioned on various joints or body portions to measure movement by joint location and type. The one or more sensors measure body and/or joint movement in 9 DOF, as described elsewhere herein. The joint-vision model 820 uses computer vision, for example using an image sensor in a mobile computing device or camera (e.g., may or may not include three-dimensional or depth information), to measure movement by joint or a movement of the entire body and, optionally, a composite body view. Additional aids such as reflective markers may be used to enhance body movement tracking. The posture-master model 830 uses outputs from one or both of the joint-sensor model 810 and the joint vision model 820, or even outputs from other models available in the art, to determine a gait type as an indication of neural, muscular, skeletal, or other health conditions.

Figures 9A, 9B, 9C:
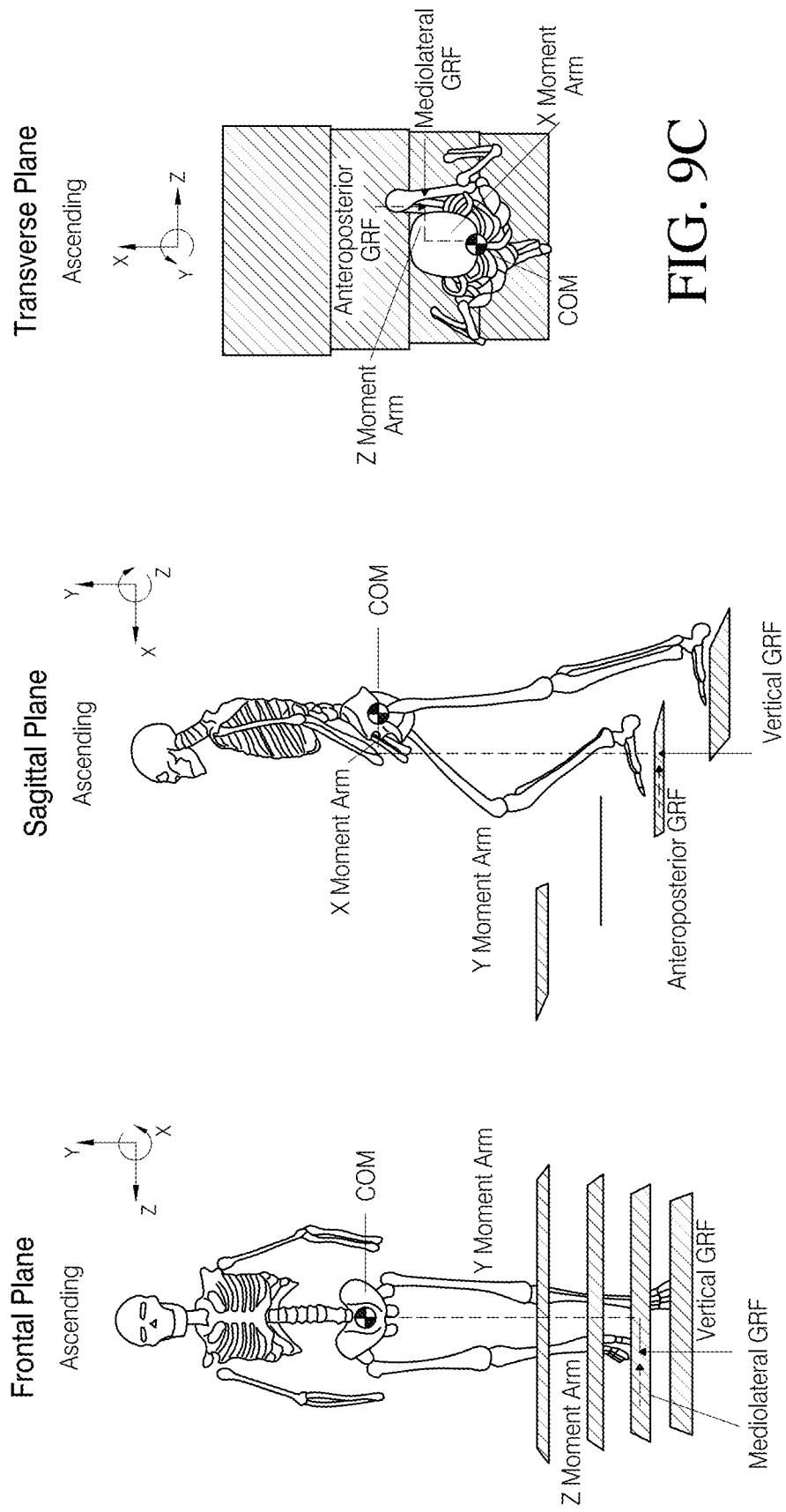
FIGS. 9A-9C illustrate various planes of movement measurement by the systems and methods described herein.

The machine learning models described herein, either alone or in combination, measure movements that involve multiple planar movements, as shown in FIGS. 9A-9C. FIG. 9A shows various movements about an X-axis; FIG. 9B shows various movements about a z-axis; and FIG. 9C shows various movements about a y-axis. For example, vertical ground reaction force (GRF) in a y-axis plane and mediolateral GRF in a z-axis plane relative to a center of mass (COM) are shown in FIG. 9A. Further for example, FIG. 9B shows a vertical GRF in a y-axis plane and an anteroposterior GRF in an x-axis plane relative to a COM. Further for example, FIG. 9C shows a mediolateral GRF in a z-axis plane and an anteroposterior GRF in an x-axis plane. The sensor system measures movement of body portions with respect to the sensor. One or more of the machine learning models then translate those sensor readings with respect to the COM of the monitored individual, as described elsewhere herein.

Figure 10C:
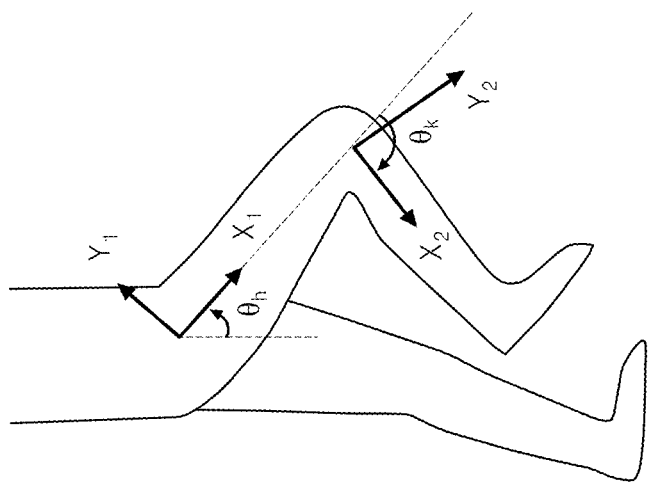
FIGS. 10A-10C illustrate various movements that are measurable by the systems and methods described herein.
Figure 10B:
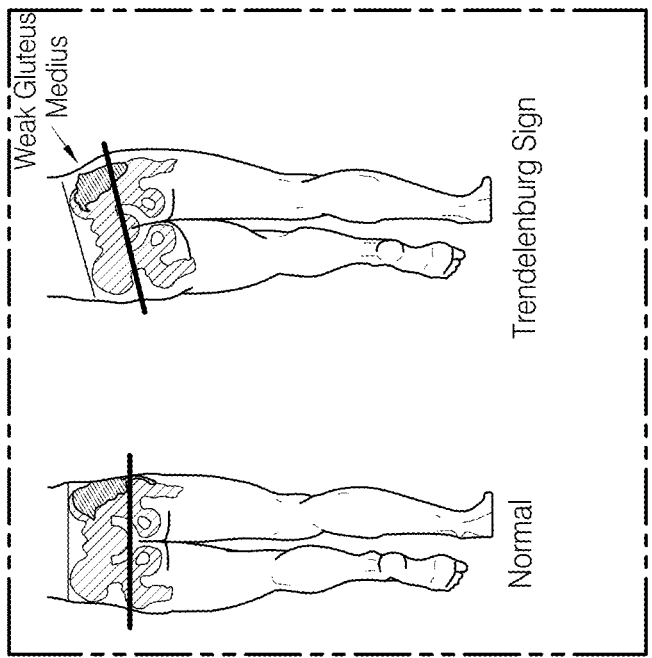
Figure 10A:
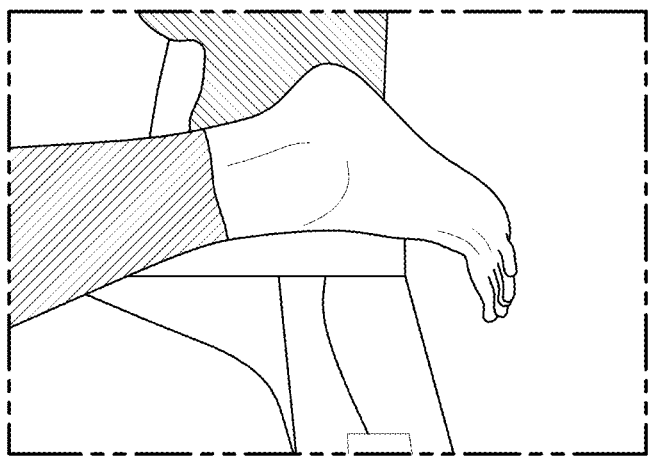

FIGS. 10A-10C show exemplary, non-limiting embodiments of movements measurable by a sensor system and processed by a joint-sensor model 810 of the present disclosure. One or more sensors are selectively positioned on a body of a user. Exemplary, non-limiting locations of sensors are: left shoulder, right shoulder, right knee, left knee, right ankle, left ankle, right toes, left toes, forehead (e.g., on or near frontal lobe), top of head (e.g., on or near the parietal lobes or an interface between the parietal lobes), back of head (e.g., on or near occipital lobe), right elbow, left elbow, right wrist, left wrist, or any combination thereof. Each sensor measures movement in 9 DOF of the body portion to which it is attached. For example, the sensor measures angular rate along the x, y, z axis (e.g., using an accelerometer)—referred to as a(x,y,z); rotation along the x, y, z axis (e.g., using a gyroscope) referred to as g(x,y,z); and force along the x, y, z axis (e.g., using a magnetometer)—referred to as m(x,y,z). The processor in the sensor, sensor system, or in the mobile computing device classifies the movement of the sensor coupled to the body portion as a direction of movement and a magnitude of the movement. The direction of movement is initially measured relative to each sensor measuring the movement. Then one or more of the machine learning models translate the direction of movement relative to a center of mass of the user so that the movement is either measured as towards or away from the center of mass in one of the three planes (sagittal, coronal, transverse).

For example, when a user is walking, the sensors measure movement at three locations, such that the model outputs the above movements in this format: <joint>, <axis>, <movement>, <range>. Exemplary joint-sensor model outputs include the following formats: toe, sagittal, plantar flexion, 10 degrees; hip, frontal, adduction, 30 degrees; and knee, sagittal, flexion, 30 degrees. For example, FIG. 10A illustrates toe movement (e.g., plantar flexion) measurable by the systems and methods described herein. For example, using an image sensor, a foot location or position is determined and then an angle of movement (e.g., angle of heel relative to floor) is measured. FIG. 10B illustrates normal and abnormal hip and/or trunk movement measurable by the systems and methods described herein. For example, using a sensor, a movement of a right hip versus a left hip is determined. If the movement of the right hip is substantially different than the left hip, the system may output an indication that one hip is compensating for movement of the other hip or other side of the body. FIG. 10C illustrates knee, hip, and/or leg movement measurable by the systems and methods described herein. For example, an image sensor or 9 DOF sensor may be used to measure movement of a leg during an activity, e.g., walking or running, such that the angle (instantaneous or over time) of the thigh or upper leg relative to the hip and/or the knee relative to the lower leg or shin may be measured. Any of the embodiments described herein can be measured by the sensor system alone or in combination. For example, embodiments shown in FIGS. 10A-10C may all be measured together, alone, or any alternative combination with or without the embodiment shown in FIG. 4B. The embodiment of FIG. 10A may be measured along with the embodiment in FIG. 10C or any other combination to get a complete picture of stability, gait, and/or balance of the monitored individual.

Figure 11:
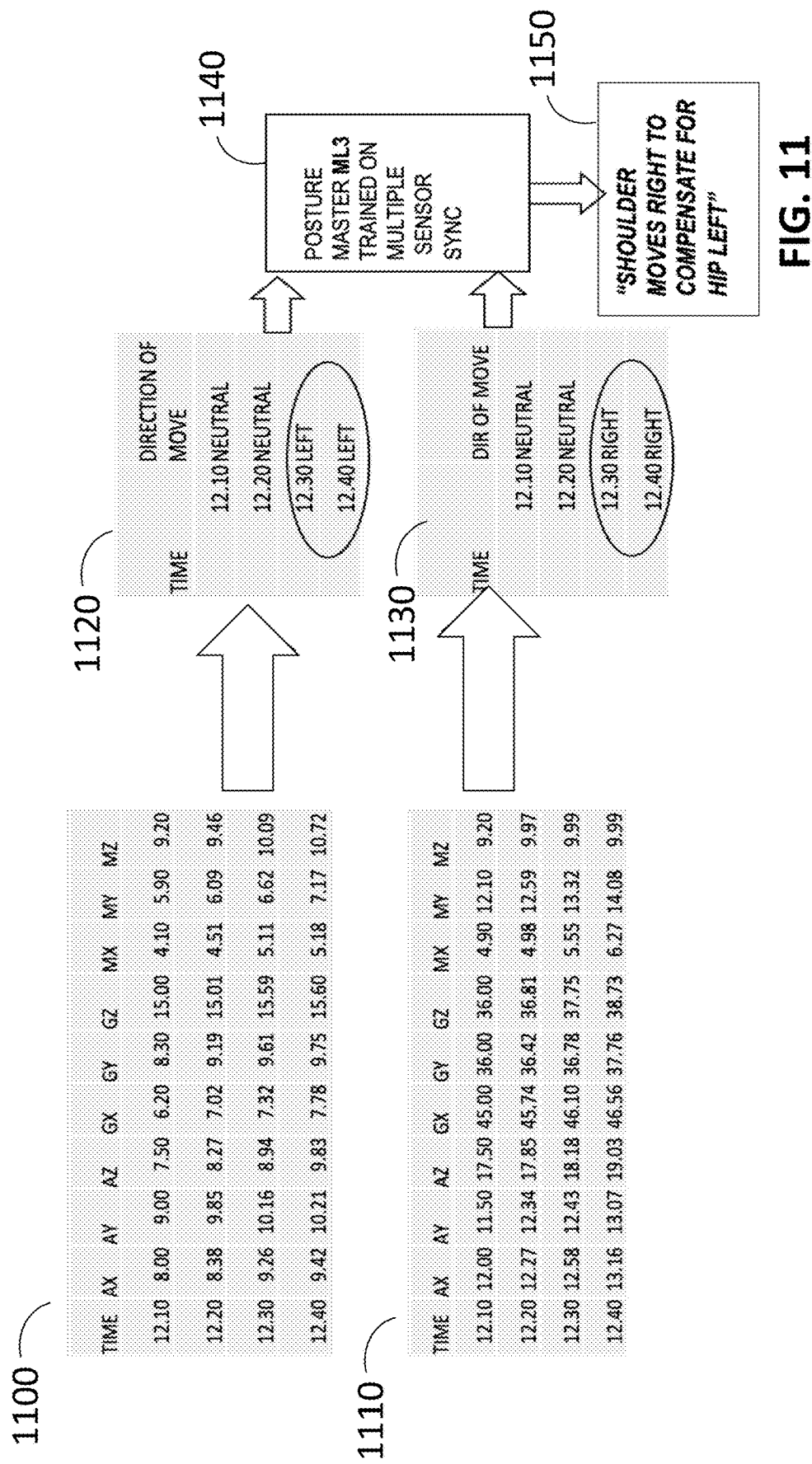
FIG. 11 illustrates an exemplary, non-limiting output of a joint-sensor model, in accordance with one or more embodiments.

Turning to FIG. 11, which shows sensor-based measurement of gait using only the joint-sensor model output 1120, 1130 as input into the posture-master model 1140, 1150. Table 1100 shows sensor data originating from a sensor positioned on a hip of the user and table 1110 shows sensor data originating from a sensor positioned on a shoulder of the same user. The data is captured over time as indicated by the time column and the data in tables 1100, 1110 are represented in 9 DOF, as described elsewhere herein and as shown in the columns labeled from left to right: AX, AY, AZ, GX, GY, GZ, MX, MY, MZ. The data in table 1100 are fed into the joint-sensor model, which outputs the data shown in table 1120 showing no directional movement of the hips at times 12.10 and 12.20 but directional movement towards the left at times 12.30 and 12.40. The data in table 1110 are fed into the joint-vision model described elsewhere herein, which outputs the data shown in table 1130 showing no directional movement of the shoulders at times 12.10 and 12.20 but directional movement of the shoulders towards the right (opposite the hips) at times 12.30 and 12.40. These data in tables 1120 and 1130 are fed into the posture master model or third machine learning model 1140, which outputs a human readable indication, for example an indication that "the shoulder moves right to compensate for hip left." Such gait is indicative of Trendelenburg gait, as described elsewhere herein.

Figures 12A, 12B, 12C, 12D:
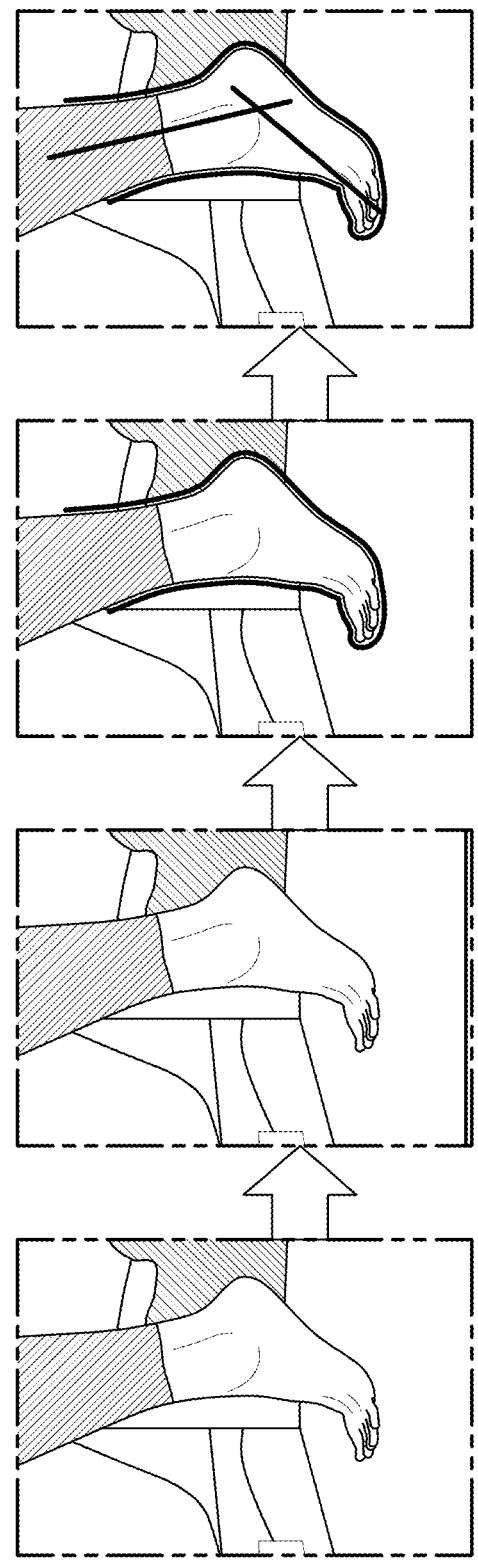
FIGS. 12A-12D illustrate visually an image processing method for training a joint-vision model, in accordance with one or more embodiments.

FIGS. 12A-12D show an exemplary movement captured using an image sensor in a mobile computing device, processed, and used to train a joint-vision model. The joint-vision model uses a modified convolutional neural network (i.e., U-Net) deep learning architecture. The details of the original U-Net architecture are shown and described in the following research article: Ronneberger, et al. "U-Net: Convolutional Networks for Biomedical Image Segmentation." Computer Science, Cornell University, 18 May 2015, the contents of which are herein incorporated by reference in their entirety. The original U-Net architecture focused on biomedical imaging applications in static images. However, the original architecture is not easily translatable to monitoring and assessing movement of an individual. As such, the model was modified to use sequences of images (e.g., up to 32 images per second) to monitor and analyze movement of an individual over time. The joint-vision model is trained to classify a plurality of image frames having one or more body portions therein, output a discrete label for the one or more body portions, and localize the one or more body portions in each image frame. The joint-vision model is trained to classify such image frames and output such discrete labels using the process defined in FIGS. 12A-12C. As shown in FIG. 12A, an image sensor of a computing device takes frames of video or images of a body portion or of movement of an individual. In this specific example shown in FIG. 12A, the individual is performing a plantar flexion movement. The frames are pre-processed to adjust for lighting and camera effects, as shown in FIG. 12B. For example, pre-processing may include converting one or more images to grayscale. Training the joint-vision model with grayscale images prevents the model from learning a bias in the learning set (e.g., only people with red pants performed sit-up, and the model learns wrongly that red pants indicate sit-ups). Alternatively, the model may be trained with one or more colored images. Further, a black white binary training mask is applied to the one or more images, with black equaling 0 and white equaling 1. A pepper-salt cleaning is done on the training mask so that any small (e.g., less than 5-pixel square) white spots are removed from the mask and only the body portions are represented in the one or more images. Pre-processing may further include trimming the one or more images and the training mask to a pre-determined size, for example 512×512. An intensity of the one or more images is standardized by computing an average intensity for all images in the set and then adjusting the intensity of each image to the average intensity. In some embodiments, one or more tags or labels may be added to the one or more body portions represented in each image to enhance body portion identification.

Figure 18A:
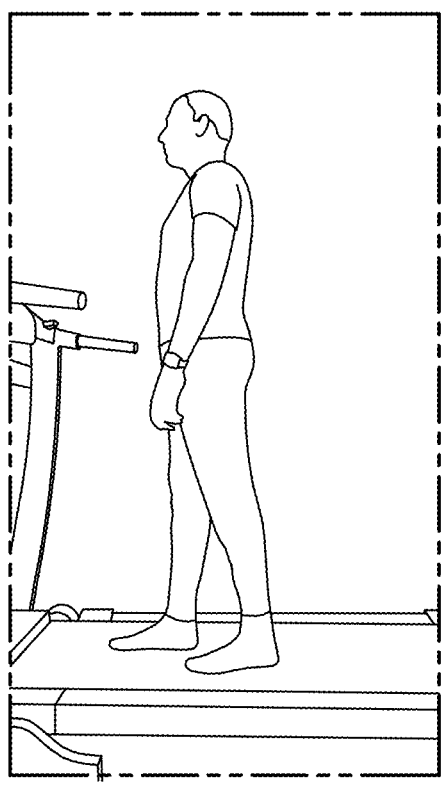
FIGS. 18A-18B illustrates an unprocessed image and a pre-processed image, respectively, use to compute a centroid of each joint.
Figure 18B:
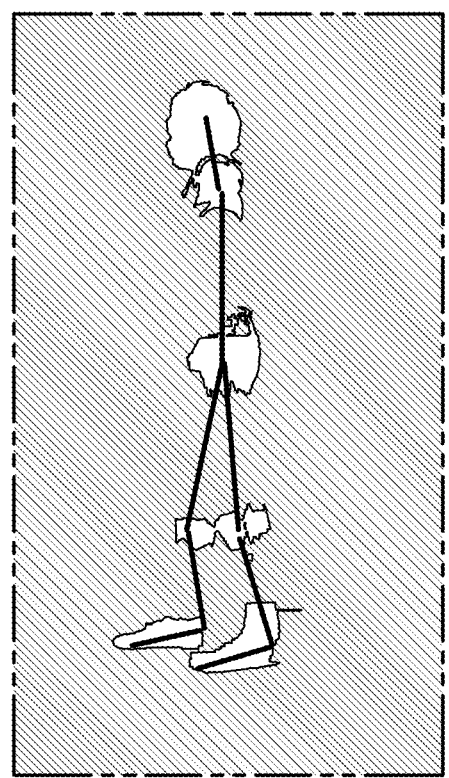

Each body part of interest is outlined, for example the foot as shown in FIG. 12C, and pixel level segmentation is performed (i.e., each pixel is classified with a label, e.g., indicating a body portion that the pixel belongs to and is give a coordinate (x, y)). This classification of pixels into a score between 1 and 0, where 1 is white and 0 is black, is also referred to as "mask". Pixel level segmentation is used to train the joint-vision model to classify body portions. A stickbox algorithm is then used to reduce the outlined body portion into a "stick figure" to determine angle and movement over time of one or more body portions, as shown in FIG. 12D and FIGS. 18A-18B. For example, as shown in FIGS. 18A-18B, a mask is applied to each body portion, as described above, and one or more centroids or geometric centers of the body portions are identified and subsequently joined via lines. The angle at each centroid is then computed.

Figure 17:
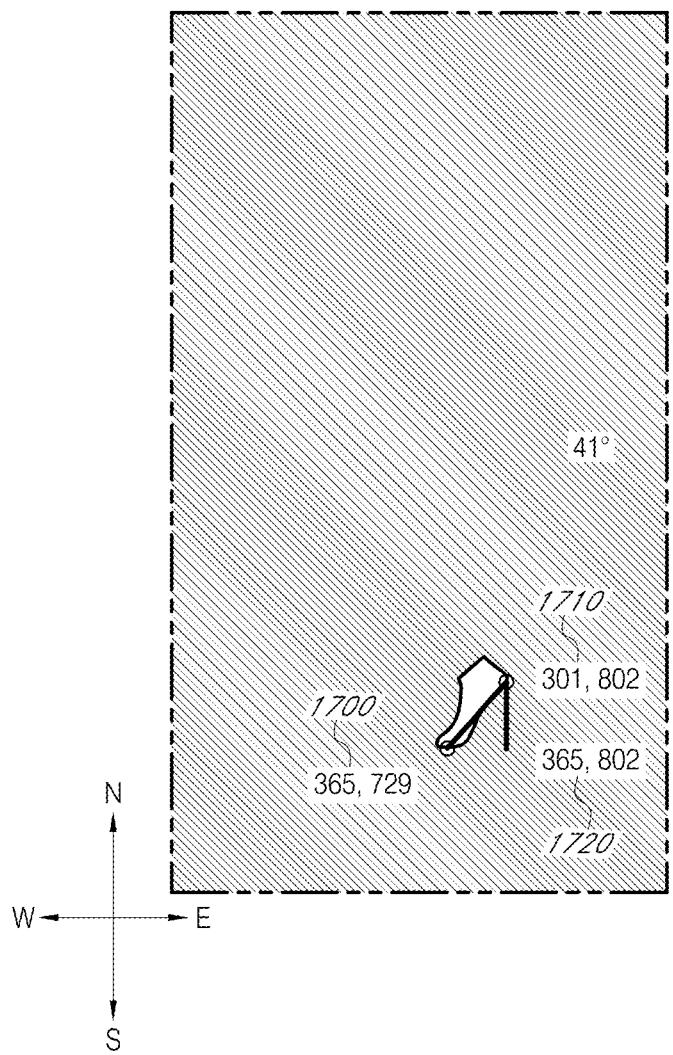
FIG. 17 illustrates a pre-processed image used to compute an angle of movement of a joint.

In some embodiments, more than one or a plurality of joint-vision models is trained on each joint separately, such that each joint-vision model may be configured to detect a particular joint. For example, the computer vision model may include a hip model, a knee model, a shoulder model, ankle joint model, etc., where each body portion is treated as a contour. The joint-vision model further includes computing a centroid for each contour (i.e., body portion) and computing a stick figure between each of the visible joints (e.g., head to shoulder, shoulder to hip, hip to knee, etc.). The angle of the joint between the two body portions is computed using trigonometry, as shown in FIG. 17. For example, the angle is calculated by determining a pair of coordinates 1700 for a southernmost white pixel and a second pair of coordinates 1710 for an easternmost white pixel; deriving a third pair of coordinates 1720; and calculating an angle between the second pair of coordinates 1710 and the third pair of coordinates 1720.

The stick figure representation of the body portion is further used to train the joint-vision model to classify and discretely label angles of joints and movements of joints over time. As such, when unprocessed images or frames are run through the joint-vision model, the model is trained to classify, discretely label, and localize the body portion and the respective angle and/or movement over time of the body portion. The trained model is then deployed to detect body portions in a series of image frames and track movement and angles associated with the tracked movement. The computer vision model takes a series of images as input and converts the images to black and white images of known dimensions (e.g., 512×512). The images are then analyzed to find a first white pixel (indicative of a body portion in the image) from top to bottom, bottom to top, left to right, and right to left. Additional parameters are in place to ensure that the first white pixel is truly indicate of a body portion and not an artifact. For example, the first white pixel should be surrounded by a majority of white pixels, not black pixels.

Figure 13A:
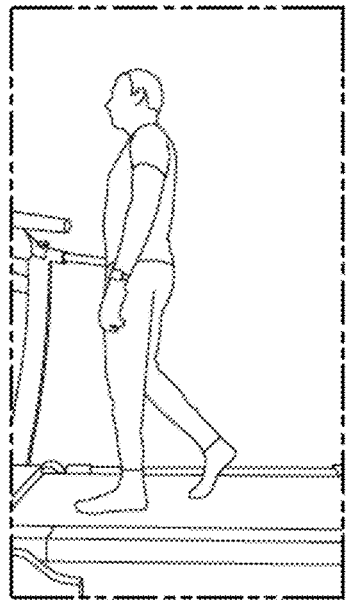
FIGS. 13A-13D illustrate an image analyzed using a joint-vision machine learning model.
Figure 13B:
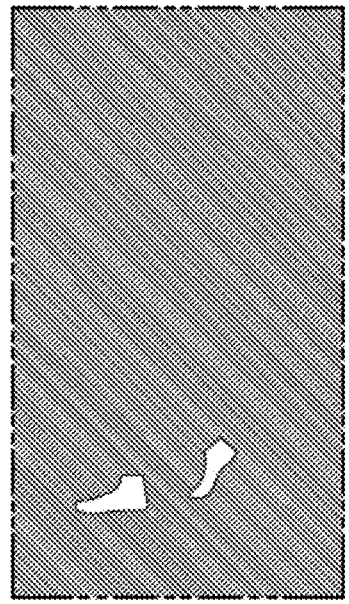
Figure 13C:
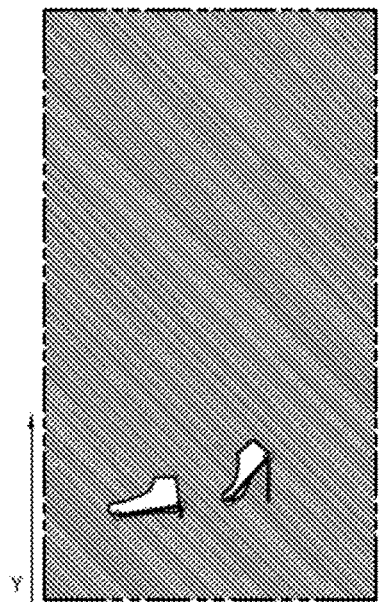
Figure 13D:
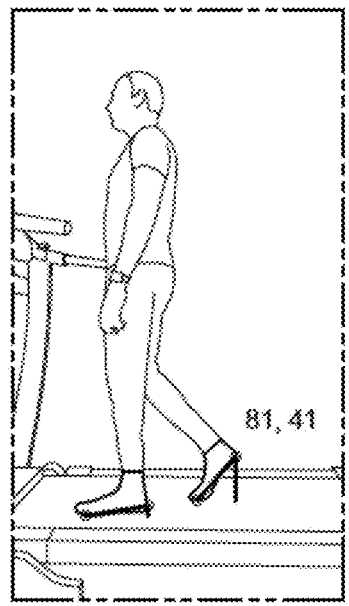
Figure 14:
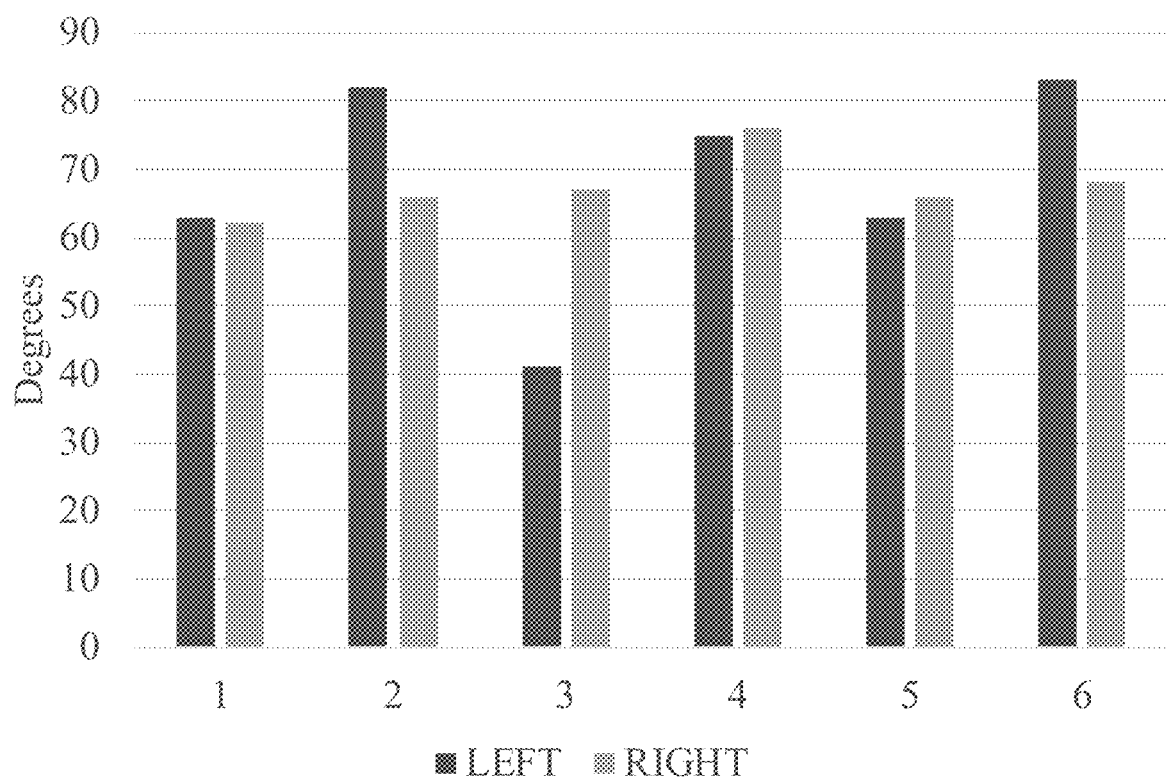
FIG. 14 is a graphical representation of an analysis of a series of images using a joint-vision machine learning model.

FIGS. 13A-13D represent an exemplary input into a joint-vision model (FIG. 13A) and an exemplary output (FIGS. 13B-13C) from the joint-vision model. Turning to FIG. 13A, a frame from a video is extracted or an image (e.g., especially comprising one frame) is used (either a single image or from a series of images). The frame displays an image of a person performing a movement or exercise, for example walking on a treadmill as shown. The joint-vision model (e.g., convolutional neural network) identifies a body portion in the image. As shown in FIG. 13B, the feet of the person are identified and the image is converted to a black and white image, using the processes described in connection with FIGS. 12A-12D and elsewhere herein. The joint-vision model then calculates an angle of the feet relative to a vertical or y-axis, as shown in FIG. 13C, using trigonometry-based algorithms. The analyzed image is then superimposed or compared to the original image and optionally annotated with movement information (e.g., measured angles) and transmitted to a second user, for example a physical therapist, doctor, neurologist, etc. The output of the joint-vision model may be represented graphically to a user, as shown in FIG. 14, as an angle of movement of the left foot over time and an angle of movement of the right foot over time. The results in FIG. 14 indicate that the left foot lifts more or is more angled relative to a y-axis than the right foot over a two-step cycle.

Returning to FIG. 8, the two models 810, 820 work in-tandem, in some instances, or alone in other instances to measure movement of a monitored individual with high accuracy. In some embodiments, models 810 and 820 function to measure similar movements using different systems (sensor vs. computer vision) and to increase the precision of system 800. The outputs of models 810, 820 are inputs into model 830, the posture master model. In some embodiments, one model of models 810, 820 is adjusted, favored, or used over the other model. For example, in some instances, one or more body portions may be obscured or not readily visible in an image frame. In currently available technologies, the processor would estimate a position or location of the body portion and adopt that position or location as truth. However, in the joint vision model 820, when a body portion is obscured or not readily visible in the image frame, the data output from the joint vision model 820 is tagged with a lower weight or degree of certainty or confidence. Model 830 then determines whether to use the data output from model 820, appropriately weighted, or whether to throw out the data from model 820 and rely instead on the data output from model 810. The training and operation of model 830 is described elsewhere herein.

Figure 15A:
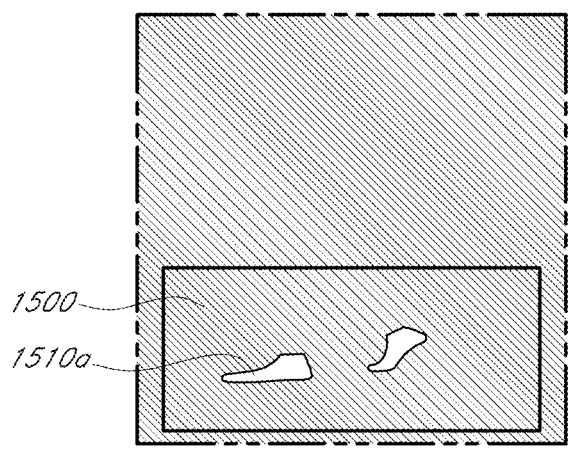
FIGS. 15A-15C illustrate various attributes that are considered in determining a confidence of data output from a joint-vision model.
Figure 15B:
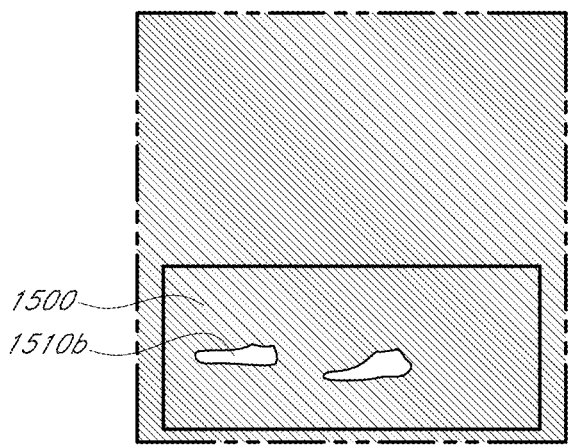
Figure 15C:
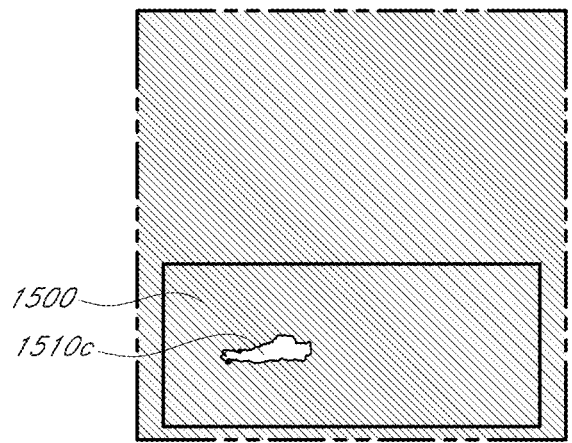

For example, the analytics system may choose to use data output from the joint-vision model or the joint-sensor model, or a weighted combination of both to determine whether or how a particular movement occurred. Various features of the models and output data are used within a regression algorithm to determine which (or both models) to use for any given instance of movement. For example, data from the joint-vision model may be used when a confidence of the output data from the joint-vision model is greater than 90% as determined by the machine learning model (e.g., neural network). The confidence for the joint-vision model is based on, at least for example, one or more of:

a shape of a body portion detected. For example, as shown in FIG. 15A, each foot appears shaped like a foot or has an expected appearance;

a detected variation of size of a body portion detected. For example, as shown in FIGS. 15A-15B, a size of each foot 1510a in FIG. 15A is relatively similar to the size of each foot 1510b in FIG. 15B. A size or area of the body portion remains relatively constant or consistent across images;

a location of a body portion should remain in a similar location as previous images of the body portion. For example, the location of the body portion in a first image should be within +/−a threshold (e.g., 5%, 10%, 5%-10%, 1%-5%, etc.) as compared to a second image or previous image. The threshold accounts for movement of the body portion that is part of the movement of the individual and not due to error or artifacts. In some embodiments, the threshold is a function of the exercise performed as well as the number of frames extracted per second. The image frame is divided into a grid (e.g., 4×4 squares), and a moving body portion and a static body portion are analyzed for their location in the image frame. For example, the static body portion is expected to be in the same square or a neighboring square in the grid. The threshold for the moving body portion is dependent on the exercise being performed. For example, during walking, the moving body portion is expected to be consistently in a bottom row of the grid. Further, for example, a head should be located at the top of an image, a foot should be located at the bottom of an image, and a head should be located above a foot in an image. As shown in FIGS. 15A-15C, the feet 1510 are always shown in a bottom portion 1500 of the image;

a model-based confidence in each pixel being classified correctly (i.e., binary-pixel of interest (e.g., body portion) is white or pixel not of interest is black) and aggregated over the entire image, to a picture level confidence. For example, each pixel is assigned a number between 0 and 1 where 1 is high confidence that the pixel belongs to the body portion and 0 is low confidence that the pixel belongs to the body portion. If the number is 0.5 (gray in the mask), it means the model is 50% sure that pixel belongs to the body portion. Thus, a perfect confidence (i.e., confidence of 1) will result in every pixel being classified as 0 (black in the mask) or 1 (white in the mask). Thus, using a confidence cutoff of 0.25 to divide the white pixels and black pixels, the average of all pixels greater than 0.25 (white) should ideally yield a confidence level of close to or substantially 1.

an acutance (i.e., sharpness) of the body portion in each image. For example, a fuzzy image of a body portion means the model struggled to define or determine where a body portion ends and where a background begins (e.g., if the movement were too slow for analysis across the series of images). As shown in FIG. 15C, the acutance of the foot 1510c is less than the acutance of foot 1510a or 1510b;

a presence or absence of all the expected body portions. For example, two feet, one head, and one hip are expected if a person is walking, as shown in FIGS. 15A-15B. If one or more expected body portions are missing or not present in an image (e.g., a person is in a crouching position) as shown in FIG. 15C, it is most likely that the locations of the one or more body portions that are seen in the image are not in a correct or expected location; and a relative length of symmetrical body portions (e.g., legs or arms or feet).

Figure 16A:
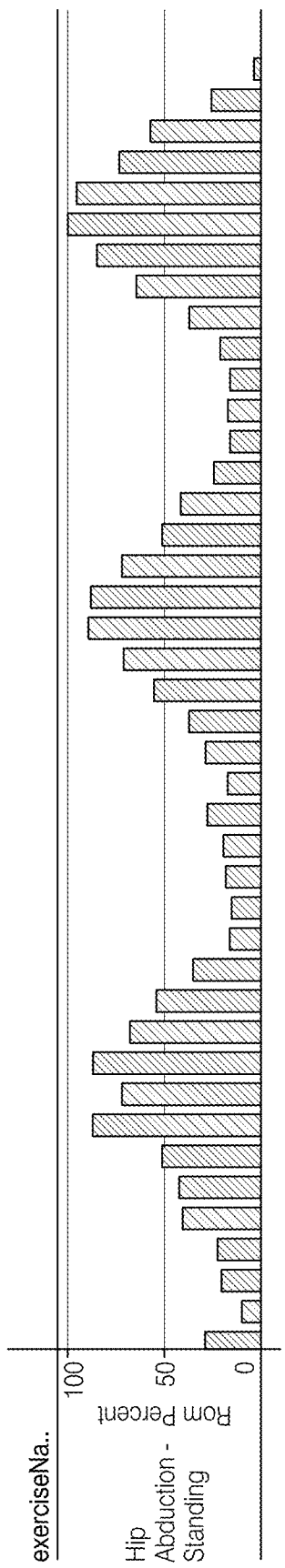
FIGS. 16A-16B illustrate a characteristic of the sensor signal that is considered in determining a confidence of data output from a joint-sensor model.
Figure 16B:
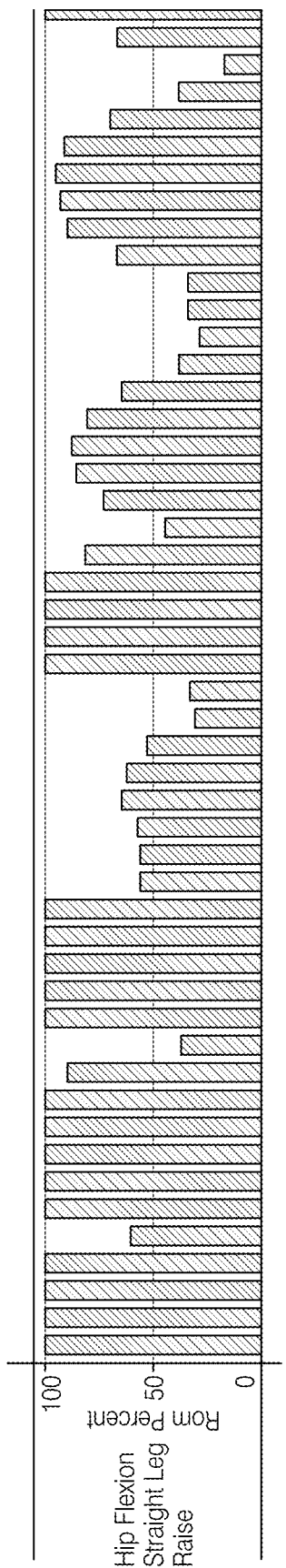

For example, data from the joint-sensor model may be used when a confidence of the output data from the joint-sensor model is greater than 90%, as determined by the posture master machine learning model described elsewhere herein. The confidence for the joint-sensor model is based on, at least for example, one or more of:

an ambient temperature as stated by manufacturer of one or more sensors;

a signal-to-noise ratio of the sensor signal. For example, a sensor emits a sensor reading n times a second. In some cases, noise in the sensor signal is expected (e.g., when a heel strikes the floor), but in most situations, there should be very little noise in the sensor signal;

a jitter in the sensor signal which is a measure of the variation of one reading to the previous reading and to the next or subsequent reading and should be within a threshold. The threshold is calculated by taking into account the parameters of an exercise to be performed. For example, the exercise to be performed takes 20 seconds for a repetition, and there are 20 readings a second. The distance moved by the limb is 40 degrees rotation or 40 inches given expected dimensions of a human. The average distance between two readings is obviously 40 degrees/(20 secs*20 readings)=1/10 degrees. Thus, the threshold is empirically derived from the exercise performed, the instructions, and/or an average of many ideal patients;

a steadiness of the signal. For example, the average (e.g., a sliding window average of n readings) should be increasing or decreasing since the patient is performing an expected movement (e.g., raising a limb and then lowering). To compute the average, a set of readings (e.g., 4 readings equaling about ⅕ a second) are input and fit to a spline (i.e., smooth curve) using known interpolation techniques. The number of roots (i.e., turning points to the smooth curve) should be ideally 1 or 2 and not more than 5 for one repetition. For example, as shown in FIGS. 16A-16B, sensor readings should follow a basic pattern of repeated bell curves or repeated substantially Gaussian distributions, as shown in FIG. 16A, which elicits a high confidence score. However, if the sensor readings display no discernible pattern, display random drops, or little repetition, as shown in FIG. 16B, then the sensor readings are given a low confidence score;

an aggregation of readings should display a smooth movement. For example, while exercising, movements are generally smooth. As can be seen in FIG. 16A, the bell curve pattern of the sensor reading shows a generally smooth or sinusoidal movement or pattern;

an expected movement of a body portion versus the sensed movement of the body portion. For example, during exercise the system expects a certain pattern of readings from the exercise being performed. For example, most exercises are movement of a hand or leg in two dimensions. If the sensor detects an unexpected three-dimensional movement (i.e., a solid angle), it may be classified as an error, since for that exercise, no 3D movement was expected.

a gyroscope reading from one or more sensors measures rotation along an axis. The integrated sensor unit includes a gyroscope and an accelerometer. In a forward walking exercise, rotation of a sensor on the belt buckle position on the hip should be close to zero. For the same walking movement, a knee moves forward and backward not left and right.

The third machine learning model or posture master model may select to use the data output from one or both of the joint-vision model and the joint-sensor model to output a gait, movement, stability, etc. of a user. The third machine learning model may, additionally or alternatively, use data output from another sensor system (e.g., cardiovascular, PPG, temperature, circumference, wearable, etc.), machine learning model, patient input data, health record, or other source, as appropriate. In some embodiments, the posture master model is a supervised model, for example a logistic regression. The inputs to the posture master model include, but are not limited to, one or more of the following: one or more features used to calculate a joint-vision model confidence (e.g., shape, variation, location, acutance, etc.) and a joint-sensor model confidence (e.g., temperature, signal-to-noise ratio, steadiness, etc.); only an input indicating a classification as acceptable or not acceptable of the vision based system (e.g., during training phase); an input indicating a classification of the sensor based system as acceptable or not acceptable (e.g., in training phase); and an input indicating which model is better for particular use cases (e.g., during a training phase, 1 equals better choice; 0 equals second choice) where a case means the set of all other inputs. Based on these same inputs, in the deployment phase, the posture master model assigns a score. In one embodiment, a logistic regression algorithm is used which emits a 0/1 score and it picks either vision or sensor. In another embodiment, a Bayesian model is used which emits a score between 0 and 1, that total of the two models equals up to 1. For example, a score of [0.6, 0.4] results in a final predicted angle of a joint equaling 0.6*angle predicted by joint-vision model plus 0.4*angle predicted by joint-sensor model.

The third machine learning model or the posture master model may further select which one or more models as inputs based on one or more of the following criteria:

a movement of two or more joints compared at a defined or predetermined time instant. For example, in hip versus knee movements, it is hard to compare sensor readings of two different joints at the same instant, whereas all joints appear in one image using an image sensor which makes it easier to compare.

a size of movement. For example, small movements are more likely to be measured by the joint-vision model and large movements are more likely to be measured by the joint-sensor model. For example, in a short movement of a few centimeters, the noise in sensor readings are large enough to drown the actual signal. There is noise from the hardware, vibrations, and even earth movement. The presence of metallic objects and electrical fields may further exacerbate this problem. Further, jitter detection in the sensor signal, described elsewhere herein cannot be applied for short movements as a result of the number of sensor readings in a short movement. For the joint-vision model, an image sensor can detect, for example, 2 cm of movement assuming the model accurately classifies each pixel;

a dimension of movement. For example, three-dimensional movement is more readily sensed by the joint-sensor model with high confidence while two-dimensional movement is more readily measured by the joint-vision model with high confidence since a camera sees in two dimensions. In some embodiments, three-dimensional movement is also or alternatively sensed by the joint-vision model, for example, when three-dimensional or depth sensor cameras are used. Note that most exercises do not require 3D movement of a body portion; only a small number of exercises require 3D movement;

a direction of movement. For example, movements along a vertical line of gravity cannot be detected by the joint-sensor model described herein. For example, when a limb is moved from position A to position B, an accelerometer in the sensor measures both acceleration of the sensor with respect to the ground as well as a gravitational force. If a patient holds a limb without movement or moves the limb with slow movement, there is no acceleration with respect to the ground. However, gravity still acts, and the sensor detects the magnitude (unchanging) and the angle of gravity. The inclination of the sensor to the gravitational axis at the starting point A and the angle at B is computed and the difference is shown as the actual rotational movement of the joint from position A to position B. If positions A and B are in the same inclination to gravity (e.g., perfectly vertical), the change cannot be detected by the sensor. In addition, at very slow speeds, the error in magnetometer becomes significant;

speed of movement. For example, long, smooth, and/or slow movement is more readily detected by the joint-sensor model with high confidence while fast movement is more readily detected by the joint-vision model with high confidence;

a number of image sensors required. The joint-vision based model performs worse than the joint-sensor model in applications where more than one image sensor is required to capture movement. For example, the image sensor has to be positioned with respect to the exercise. Image sensors cannot sense depth of movement or body portions. An image sensor can sense up/down and left/right movement but cannot sense forward/backward directly but only detects it as a change of the person's height; and a background color. For example, as wall behind a user could be the same or substantially the same color (e.g., black) as the clothes worn by the user (e.g., black), which increases error for the joint-vison model, since there is little or no contrast between the user and wall.

One aspect of the present disclosure is directed to a system for assessing movement of one or more body portions, comprising one or more inertial sensors positioned on one or more body portions; an image sensor; a processor communicatively coupled to the one or more inertial sensors and the image sensor; and a memory, coupled to the processor, configured to store program instructions, wherein, when executed by the processor, the program instructions cause the processor to perform a method.

In any of the preceding embodiments, a first machine learning model performs a method including: receiving a sensor signal using the one or more inertial sensors, the sensor signal indicative of movement of the one or more body portions over a time period, analyzing the sensor signal of the one or more body portions to determine a movement of the one or more body portions, and determining a sensor confidence level based, at least in part, on a characteristic of the sensor signal over the time period.

In any of the preceding embodiments, the first machine learning model or a second machine learning model performs a method including: receiving a series of images using the image sensor, the series of images comprising the one or more body portions depicted therein and indicative of movement of the one or more body portions over the time period, identifying the one or more body portions in each of the series of images, measuring an angle of movement of the one or more body portions in each of the series of images over the time period, and determining a vision confidence level based, at least in part, on an ability of the first or second machine learning model to identify the one or more body portions in each of the series of images.

In any of the preceding embodiments, the first, second, or a third machine learning model is further configured to perform a method including: selecting the sensor signal, the measured angle of movement, or a combination thereof as an input into the first, second, or third machine learning model based on the sensor confidence level and the vision confidence level, respectively, analyzing the input to determine a movement pattern of the one or more body portions, and outputting the movement pattern to a user.

In any of the preceding embodiments, the characteristic of the sensor signal comprises a smoothness of the sensor signal over the time period.

In any of the preceding embodiments, the smoothness comprises a substantially sinusoidal pattern.

In any of the preceding embodiments, the characteristic comprises a degree of rotation sensed by the one or more sensors when positioned in parallel to a plane of movement.

In any of the preceding embodiments, the sensor confidence level is further based on an expected movement of the one or more body portions versus an actual movement of the one or more body portions.

In any of the preceding embodiments, the vision confidence level is further based on one or more attributes of the identified body portions in the series of images.

In any of the preceding embodiments, the one or more attributes include one or more of: a shape of the identified one or more body portions, a relative size of the identified one or more body portions, a location in each image of the identified one or more body portions, an acutance in each image of the identified one or more body portions, a comparative length of symmetrical body portions, and a combination thereof.

In any of the preceding embodiments, the vision confidence level is further based on a binary classification of each pixel in each of the series of images.

In any of the preceding embodiments, the vision confidence level is further based on an expected number of body portions in each image equaling an actual number of body portions in each image.

In any of the preceding embodiments, the movement detected by the one or more sensors comprises movement in three-dimensions.

In any of the preceding embodiments, the movement detected by the one or more sensors comprises movement in nine degrees-of-freedom.

In any of the preceding embodiments, one or more of the first machine learning model, the second machine learning model, and the third machine learning model is a neural network.

Another aspect of the present disclosure is directed to a system for assessing movement of one or more body portions, including: an image sensor; a processor communicatively coupled to the image sensor; and a memory, coupled to the processor, configured to store program instructions, wherein, when executed by the processor, the program instructions cause the processor to perform a method.

In any of the preceding embodiments, the method performed by a first machine learning model includes: receiving a series of images using the image sensor, the series of images comprising the one or more body portions depicted therein and indicative of movement of the one or more body portions over a time period, identifying the one or more body portions in each of the series of images, measuring an angle of movement of the one or more body portions in each of the series of images over the time period, and determining a vision confidence level based, at least in part, on an ability of the joint-vision machine learning model to identify the one or more body portions in each of the series of images.

In any of the preceding embodiments, the first or a second machine learning model performs the method comprising: receiving the measured angle of movement as an input into the first or second master machine learning model based on the vision confidence level, analyzing the input to determine a movement pattern of the one or more body portions, and outputting the movement pattern to a user.

In any of the preceding embodiments, the system further includes a mobile computing device comprising the image sensor, the processor, and the memory.

In any of the preceding embodiments, the vision confidence level is further based on one or more attributes of the identified body portions in the series of images.

In any of the preceding embodiments, the one or more attributes include one or more of: a shape of the identified one or more body portions, a relative size of the identified one or more body portions, a location in each image of the identified one or more body portions, an acutance in each image of the identified one or more body portions, a comparative length of symmetrical body portions, and a combination thereof.

In any of the preceding embodiments, the vision confidence level is further based on a binary classification of each pixel in each of the series of images.

In any of the preceding embodiments, the vision confidence level is further based on an expected number of body portions in each image equaling an actual number of body portions in each image.

In any of the preceding embodiments, the joint-vision machine learning model is a convolutional neural network.

In any of the preceding embodiments, identifying the one or more body portions in each image comprises identifying a first white pixel as each image is analyzed from top to bottom, bottom to top, left to right, and right to left.

One aspect of the present disclosure is directed to a system for assessing movement of one or more body portions, comprising one or more inertial sensors positioned on one or more body portions; a processor communicatively coupled to the one or more inertial sensors; and a memory, coupled to the processor, configured to store program instructions, wherein, when executed by the processor, the program instructions cause the processor to perform a method.

In any of the preceding embodiments, a first machine learning model performs a method including: receiving a sensor signal using the one or more inertial sensors, the sensor signal indicative of movement of the one or more body portions over a time period, analyzing the sensor signal of the one or more body portions to determine a movement of the one or more body portions, and determining a sensor confidence level based, at least in part, on a characteristic of the sensor signal over the time period.

In any of the preceding embodiments, a first, second, or third machine learning model is further configured to perform a method including: selecting the sensor signal as an input into the first, second, or third machine learning model based on the sensor confidence level, analyzing the input to determine a movement pattern of the one or more body portions, and outputting the movement pattern to a user.

In any of the preceding embodiments, the characteristic of the sensor signal comprises a smoothness of the sensor signal over the time period.

In any of the preceding embodiments, the smoothness comprises a substantially sinusoidal pattern.

In any of the preceding embodiments, the characteristic comprises a degree of rotation sensed by the one or more sensors when positioned in parallel to a plane of movement.

In any of the preceding embodiments, the sensor confidence level is further based on an expected movement of the one or more body portions versus an actual movement of the one or more body portions.

In any of the preceding embodiments, the movement detected by the one or more sensors comprises movement in three-dimensions.

In any of the preceding embodiments, the movement detected by the one or more sensors comprises movement in nine degrees-of-freedom.

In any of the preceding embodiments, one or more of the first machine learning model, the second machine learning model, and the third machine learning model is a neural network.

In any of the preceding embodiments, all or a subset of the method may be performed by one, two, or three machine learning models.

The examples and illustrations included herein show, by way of illustration and not of limitation, specific embodiments in which the subject matter may be practiced. Other embodiments may be utilized and derived therefrom, such that modifications may be made without departing from the scope of this disclosure. This disclosure is intended to cover any and all adaptations or variations of various embodiments, and it will be readily apparent to those of ordinary skill in the art, in light of the teachings of these embodiments, that numerous changes and modifications may be made without departing from the spirit or scope of the appended claims.

What is claimed is:

1. A computer-implemented method for monitoring a gait associated with one or more lower extremities, the method comprising:
   receiving image data captured by one or more image sensors, the image data including a plurality of images depicting one or more lower extremities moving based on a care protocol and over a time period;
   receiving inertial sensor data from one or more inertial sensors positioned on the one or more lower extremities;
   receiving computer vision data including data representing at least a portion of the one or more lower extremities;
   correlating the computer vision data over the time period with the received image data corresponding to the received inertial sensor data;
   identifying, based on the correlation, the one or more lower extremities;
   measuring, based on the image data or the computer vision data, one or more gait parameters associated with the identified one or more lower extremities moving during the time period;
   determining, based on the one or more gait parameters, a movement pattern of the one or more lower extremities;
   determining a sensor confidence level based on one or more characteristics of the inertial sensor data;
   determining an updated movement pattern or an updated gait condition based on the one or more characteristics of the inertial sensor data in response to determining that the sensor confidence level is above a predefined threshold;
   outputting the updated movement pattern or the updated gait condition of the one or more lower extremities; and
   adjusting the care protocol for a user based on the output.

2. The computer-implemented method of claim 1, wherein the one or more lower extremities comprise: one or more legs, one or more knees, one or more ankles, one or more feet, or one or more toes.

3. The computer-implemented method of claim 1, wherein the one or more gait parameters comprise, stance time, swing time, step length, step width, and joint angle.

4. The computer-implemented method of claim 1, wherein the determined movement pattern comprises a hyperextension, a Trendelenburg gait, a hemiplegic gait, a diplegic gait, an antalgic gait, or an ataxic side based gait.

5. The computer-implemented method of claim 1, wherein the gait condition comprises an indication of a neural, a muscular, or a skeletal health condition determined according to the movement pattern.

6. The computer-implemented method of claim 1, further comprising:
   analyzing the inertial sensor data received from one or more inertial sensors positioned on the one or more lower extremities during the movement over the time period.

7. The computer-implemented method of claim 1, wherein the output further comprises an alert that includes an instruction to consult a healthcare provider.

8. The computer-implemented method of claim 1, wherein the one or more gait parameters comprise balance measurements associated with symmetry of heel strikes, symmetry of toe offs from ground, or a rotation of one or more lower extremity.

9. A system for assessing gait associated with one or more body portions, comprising:
   an image sensor configured to obtain image data comprising a plurality of images depicting the one or more body portions performing movement over a time period and based on a care protocol;
   a computer vision model configured to obtain computer vison data including data representing at least a portion of the one or more body portions performing the movement over the time period;
   one or more inertial sensors positioned on the one or more body portions and configured to receive inertial sensor data from one or more inertial sensors;
   a processor configured to:
      correlate the computer vision data over the time period with the received image data corresponding to the received inertial sensor data
      identify based on the correlation, the one or more body portions;
      measure, based on the image data or the computer vision data, one or more gait parameters associated with the identified one or more body portions moving over the time period;
      determine, based on the movements over the time period and the one or more gait parameters, a movement pattern of the one or more body portions;
      determine a sensor confidence level based on one or more characteristics of the inertial sensor data;
      determine an updated movement pattern or an updated gait condition based on the one or more characteristics of the inertial sensor data in response to determining that the sensor confidence level is above a predefined threshold;
      output the updated movement pattern or the updated gait condition of the one or more body portions; and
      adjusting the care protocol for a user based on the output.

10. The system of claim 9, wherein the one or more body portions comprise: one or more legs, one or more knees, one or more ankles, one or more feet, or one or more toes.

11. The system of claim 9, wherein the one or more gait parameters comprise, stance time, swing time, step length, step width, and joint angle.

12. The system of claim 9, wherein the determined movement pattern comprises a hyperextension, a Trendelenburg gait, a hemiplegic gait, a diplegic gait, an antalgic gait, or an ataxic side based gait.

13. The system of claim 9, wherein the gait condition comprises an indication of a neural, a muscular, or a skeletal health condition determined according to the movement pattern.

14. The system of claim 9, wherein the output further comprises an alert that includes an instruction to consult a healthcare provider.

15. The system of claim 9, wherein the one or more gait parameters comprise balance measurements associated with symmetry of heel strikes, symmetry of toe offs from ground, or a rotation of one or more lower extremity.

16. A non-transitory computer-readable medium encoded with instructions, that when executed by one or more processors, cause the one or more processors to execute a process for monitoring a gait associated with one or more lower extremities, the instructions comprising:
   receiving image data captured by one or more image sensors, the image data including a plurality of images depicting one or more lower extremities moving based on a care protocol and over a time period;
   receiving inertial sensor data from one or more inertial sensors positioned on the one or more lower extremities;
   receiving computer vision data including data representing at least a portion of the one or more lower extremities;
   correlating the computer vision data over the time period with the received image data corresponding to the received inertial sensor data;
   identifying, based on the correlation, the one or more lower extremities;
   measuring, based on the image data or the computer vision data, one or more gait parameters associated with the identified one or more lower extremities moving during the time period;
   determining, based on the one or more gait parameters, a movement pattern of the one or more lower extremities;
   determining a sensor confidence level based on one or more characteristics of the inertial sensor data;
   determining an updated movement pattern or an updated gait condition based on the one or more characteristics of the inertial sensor data in response to determining that the sensor confidence level is above a predefined threshold;
   outputting the updated movement pattern or the updated gait condition of the one or more lower extremities; and
   adjusting the care protocol for a user based on the output.

17. The computer-readable medium of claim 16, wherein the one or more lower extremities comprise: one or more legs, one or more knees, one or more ankles, one or more feet, or one or more toes.

18. The computer-readable medium of claim 16, wherein the one or more gait parameters comprise, stance time, swing time, step length, step width, and joint angle.

19. The computer-readable medium of claim 16, wherein the determined movement pattern comprises a hyperextension, a Trendelenburg gait, a hemiplegic gait, a diplegic gait, an antalgic gait, or an ataxic side based gait.

20. The computer-readable medium of claim 16, further comprising:
   analyzing the inertial sensor data received from one or more inertial sensors positioned on the one or more lower extremities during the movement over the time period.

* * * * *